(12) United States Patent
Harada

(10) Patent No.: US 7,378,672 B2
(45) Date of Patent: May 27, 2008

(54) PARTICLE BEAM THERAPEUTIC APPARATUS

(75) Inventor: Hisashi Harada, Tokyo (JP)

(73) Assignee: Mitsubishi Denki Kabushiki Kaisha, Chiyoda-Ku, Tokyo (JP)

( * ) Notice: Subject to any disclaimer, the term of this patent is extended or adjusted under 35 U.S.C. 154(b) by 280 days.

(21) Appl. No.: 11/242,086

(22) Filed: Oct. 4, 2005

(65) Prior Publication Data

US 2006/0231775 A1    Oct. 19, 2006

(30) Foreign Application Priority Data

Apr. 13, 2005    (JP)    ............................. 2005-115819

(51) Int. Cl.
     *A61N 5/00*      (2006.01)
     *G21G 5/00*      (2006.01)

(52) U.S. Cl. ............................. 250/492.3; 250/493.1; 250/505.1; 250/515.1; 250/503.1; 250/359.1; 378/65; 378/147; 378/152; 313/359.1

(58) Field of Classification Search ............. 250/493.1, 250/492.3, 505.1, 515.1, 503.1, 359.1; 378/65, 378/147, 152; 313/359.1
See application file for complete search history.

(56) References Cited

U.S. PATENT DOCUMENTS

| | | | |
|---|---|---|---|
| 4,110,623 A | 8/1978 | Azam et al. | |
| 5,012,111 A | 4/1991 | Ueda | |
| 6,034,377 A | 3/2000 | Pu | |
| 6,040,236 A | 3/2000 | Aiso | ............. 438/486 |
| 6,051,453 A | 4/2000 | Takemura | ............. 438/166 |
| 6,165,875 A | 12/2000 | Fonash et al. | ............. 438/486 |
| 6,268,610 B1 | 7/2001 | Pu | |
| 6,462,490 B1 | 10/2002 | Matsuda et al. | |
| 2006/0022152 A1* | 2/2006 | Natori et al. | ............. 250/493.1 |

FOREIGN PATENT DOCUMENTS

| | | |
|---|---|---|
| DE | 101 09 193 | 2/2002 |
| EP | 0 858 080 | 8/1998 |
| FR | 1 251 686 | 1/1961 |

(Continued)

OTHER PUBLICATIONS

Machine translated version of Komori et al. (JP2005103255 A) and English abstract.*

(Continued)

*Primary Examiner*—Jack I. Berman
*Assistant Examiner*—Meenakshi S Sahu
(74) *Attorney, Agent, or Firm*—Buchanan Ingersoll & Rooney PC

(57) ABSTRACT

A particle beam therapeutic apparatus can ensure the uniformity of dose distribution by overlapping the desired loci of the irradiation of a particle beam a reduced number of times. A flow of a particle beam transported so as to be irradiated to a diseased part is caused to deflect in two mutually orthogonal directions perpendicular to the direction of travel of the particle beam. The irradiation position of the particle beam is scanned, upon each period, in a manner to return to a position of irradiation located at the start of the period, whereby a plurality of loci drawn within one period are overlapped with one another thereby to irradiate a desired planned dose to the diseased part. The particle beam can be interrupted only at the end of the period.

9 Claims, 24 Drawing Sheets

FOREIGN PATENT DOCUMENTS

JP        2005103255 A  *  4/2005

OTHER PUBLICATIONS

Masataka Komori et al., "Optimization of Spiral-Wobbler System For Heavy-Ion Radiotherapy", Japanese Journal of Applied Physics, vol. 43, No. 9A, 2004, pp. 6463-6467.

W.T. Chu et al., "Instrumentation For Treatment of Cancer Using Proton and Light-Ion Beams", Review of Scientific Instruments, 64(8), Aug. 1993, pp. 2055-2096.

U.S. Appl. No. 10/762,244, filed Jan. 23, 2004, Harada.

* cited by examiner

FIG.2

| POINTER | ADDRESS | EXCITING CURRENT DESIGNATED VALUE | | SPIRAL PERIOD END BIT |
|---|---|---|---|---|
| | | X AXIS | Y AXIS | |
| | 0000 | $X_1$ | $Y_1$ | 0 |
| | 0001 | $X_2$ | $Y_2$ | 0 |
| → | 0002 | $X_3$ | $Y_3$ | 0 |
| | | | | |
| | | | | |
| | 0199 | $X_{200}$ | $Y_{200}$ | 1 |
| | 0200 | $X_{201}$ | $Y_{201}$ | 0 |
| | 0201 | $X_{202}$ | $Y_{202}$ | 0 |
| | | | | |
| | | | | |
| | 0399 | $X_{400}$ | $Y_{400}$ | 1 |
| | 0400 | $X_{401}$ | $Y_{401}$ | 0 |
| | 0401 | $X_{402}$ | $Y_{402}$ | 0 |
| | | | | |
| | | | | |
| | 0599 | $X_{600}$ | $Y_{600}$ | 1 |
| | 0600 | $X_{601}$ | $Y_{601}$ | 0 |
| | | | | |
| | | | | |
| | 0799 | $X_{800}$ | $Y_{800}$ | 1 |
| | | | | |

FIG.5

| POINTER | ADDRESS | EXCITING CURRENT DESIGNATED VALUE | |
|---|---|---|---|
| | | X AXIS | Y AXIS |
| | 0000 | $X_1$ | $Y_1$ |
| | 0001 | $X_2$ | $Y_2$ |
| → | 0002 | $X_3$ | $Y_3$ |
| | | | |
| | | | |
| | 0199 | $X_{200}$ | $Y_{200}$ |
| | 0200 | $X_{201}$ | $Y_{201}$ |
| | 0201 | $X_{202}$ | $Y_{202}$ |
| | | | |
| | | | |
| | 0399 | $X_{400}$ | $Y_{400}$ |
| | 0400 | $X_{401}$ | $Y_{401}$ |
| | 0401 | $X_{402}$ | $Y_{402}$ |
| | | | |
| | | | |
| | 0599 | $X_{600}$ | $Y_{600}$ |
| | 0600 | $X_{601}$ | $Y_{601}$ |
| | | | |
| | | | |
| | 0799 | $X_{800}$ | $Y_{800}$ |
| | | | |

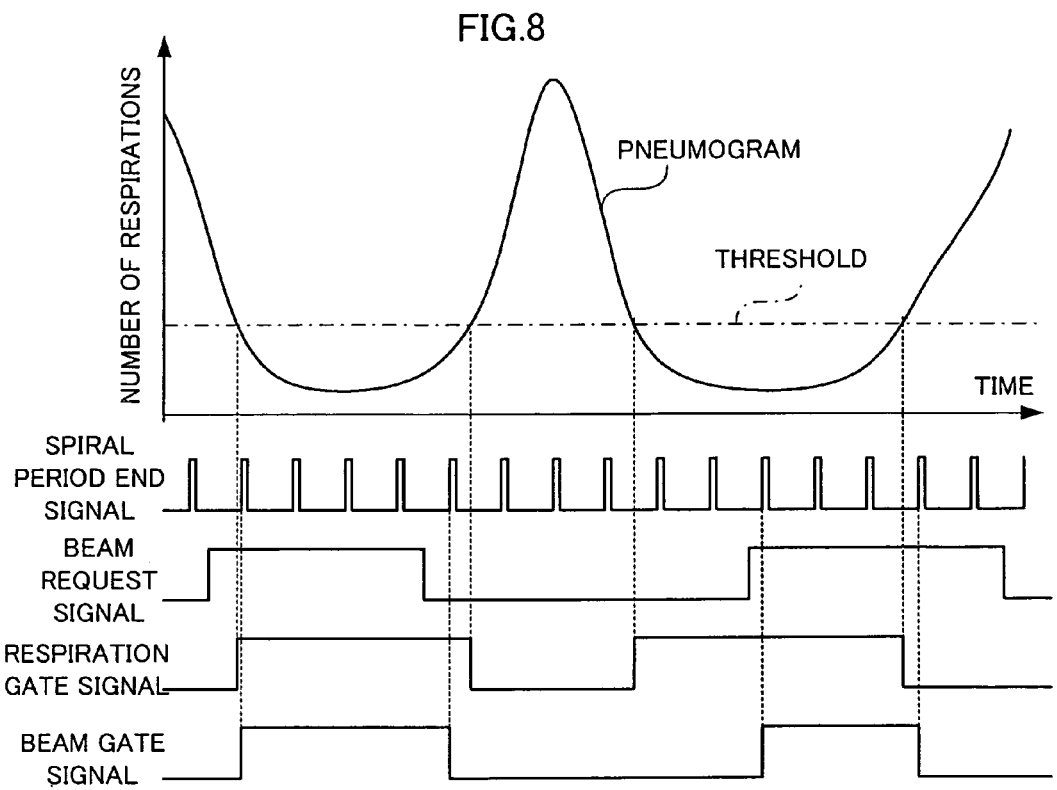
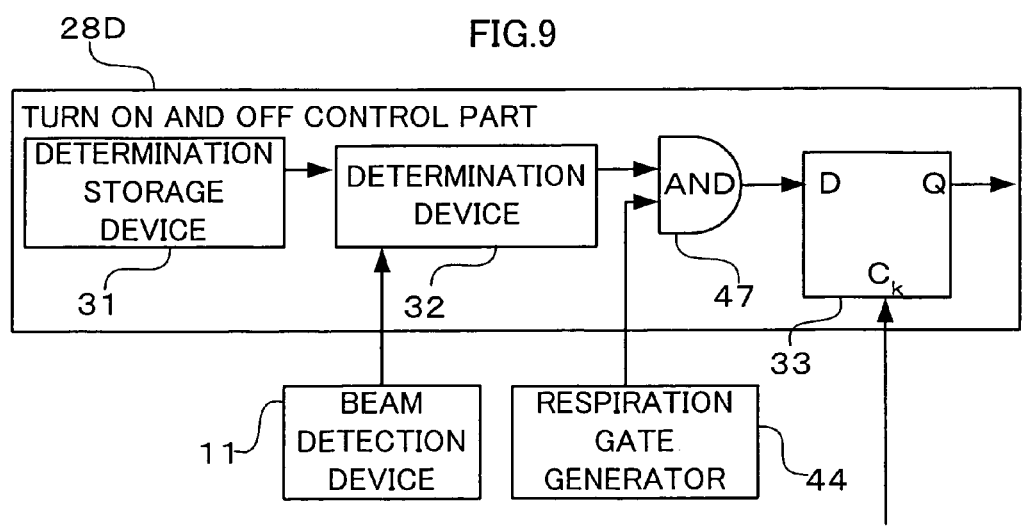

FIG.11

| POINTER | ADDRESS | AMPLITUDE DATA | SPIRAL PERIOD END BIT |
|---|---|---|---|
| | 0000 | $B_1$ | 0 |
| | 0001 | $B_2$ | 0 |
| → | 0002 | $B_3$ | 0 |
| | | | |
| | | | |
| | 0199 | $B_{200}$ | 1 |

FIG.12

| X POINTER | Y POINTER | ADDRESS | SINE WAVE DATA |
|---|---|---|---|
| | | 0000 | $PH_1$ |
| | | 0001 | $PH_2$ |
| → | | 0002 | $PH_3$ |
| | | | |
| | | | |
| | → | 0090 | $PH_{91}$ |
| | | | |
| | | | |
| | | 0359 | $PH_{360}$ |

| POINTER | ADDRESS | X-AXIS ADDRESS | Y-AXIS ADDRESS |
|---|---|---|---|
| | 0000 | $XADR_1$ | $YADR_1$ |
| | 0001 | $XADR_2$ | $YADR_2$ |
| → | 0002 | $XADR_3$ | $YADR_3$ |
| | | | |
| | | | |
| | 020 | $XADR_{21}$ | $YADR_{21}$ |

| POINTER | ADDRESS | EXCITING CURRENT DESIGNATED VALUE | | WOBBLER PERIOD END BIT |
|---|---|---|---|---|
| | | X AXIS | Y AXIS | |
| | 0000 | $X_1$ | $Y_1$ | 0 |
| | 0001 | $X_2$ | $Y_2$ | 0 |
| → | 0002 | $X_3$ | $Y_3$ | 0 |
| | | | | |
| | | | | |
| | 0035 | $X_{36}$ | $Y_{36}$ | 1 |

PARTICLE BEAM THERAPEUTIC APPARATUS

BACKGROUND OF THE INVENTION

1. Field of the Invention

The present invention relates to a particle beam therapeutic apparatus capable of irradiating a planned dose by repeating the irradiation of a particle beam onto a diseased part.

2. Description of the Related Art

As a process of forming the irradiation field of a particle beam in a conventional particle beam therapeutic apparatus, there have been known a single painting method of performing irradiation over an entire diseased part by moving the position of irradiation of a particle beam each time a desired planned dose at a desired position is reached (see, for example, a first patent document: Japanese patent application laid-open No. 2002-191709) and a repainting method of irradiating a desired planned dose by scanning the position of irradiation of a particle beam in an amount of dose equal to one severalth of a desired planned dose so as to trace a predetermined track or locus with respect to a target area in such manner that the tracks or loci of the particle beam thus irradiated are repeatedly overlapped one another (see, for example, a first non-patent document: Masataka Komori, et al, "Optimization of Spiral-Wobbler System for Heavy-Ion Radiotherapy", "Japanese Journal of Applied Physics", 2004, Vol. 43, No. 9A, pp. 6463-6467).

As a track or locus employed in the repainting method, there are a circular track drawn by the point of a rotating vector with a fixed magnitude as in a wobbler method, and a spiral track drawn by the point of a rotating vector whose magnitude is modulated according to a function of the square root of time as in a spiral wobbler method.

In this spiral wobbler method, spiral tracks or loci are drawn so as to raise the uniformity of dose distribution as compared with the wobbler method. In this case, in order to scan the position of irradiation of the particle beam by applying magnetic fields to the particle beam in two axis directions (hereinafter referred to as an X-axis direction and a Y-axis direction) orthogonal to the direction of travel of the particle beam, excitation currents $I_X$, $I_Y$ obtained from the following expressions (1) through (4) are supplied to two electromagnets to be magnetized in orthogonal directions. The magnitude of the X-axis exciting current $I_X$ changes according to the product of a value that varies from 0 to 0 passing through a maximum value in a spiral period $T_S$ and a value that varies according to a sine function of a wobbler angular velocity $\omega$. Also, the magnitude of the Y-axis exciting current $I_Y$ changes according to the product of a value that varies from 0 to 0 passing through a maximum value in the spiral period $T_S$ and a value that varies according to a cosine function of the wobbler angular velocity $\omega$.

$$I_X = A\sqrt{\frac{2(t - nT_S)}{T_S}} \sin(\omega t + \phi_0) \tag{1}$$

where $nT_S \leq t < (n + 0.5)T_S$ $$I_X = A\sqrt{\frac{2\{(n + 1)T_S - t\}}{T_S}} \sin(\omega t + \phi_0) \tag{2}$$

where $(n + 0.5)T_S \leq t < (n + 1)T_S$ $$I_Y = A\sqrt{\frac{2(t - nT_S)}{T_S}} \cos(\omega t + \phi_0) \tag{3}$$

where $nT_S \leq t < (n + 0.5)T_S$ $$I_Y = A\sqrt{\frac{2\{(n + 1)T_S - t\}}{T_S}} \cos(\omega t + \phi_0) \tag{4}$$

where $(n + 0.5)T_S \leq t < (n + 1)T_S$

However, in the spiral wobbler method, a planned dose is irradiated by overlapping the spiral track or locus drawn in each spiral period $T_S$ one over another a desired number or frequency of spiral periods, and the position of each spiral locus thus overlapped is decided by the phase of a corresponding spiral period at its start time point. Accordingly, in order to ensure the uniformity of dose distribution, it is necessary to make the phase of each overlapped spiral locus at the start time point of each spiral period vary in a uniform manner. However, the phase of each spiral locus (hereinafter referred to as a spiral phase) $\phi$ at the spiral period start time point is obtained from the following expression (5), so it is uniquely decided by the spiral period $T_S$, the wobbler angular velocity $\omega$, an initial spiral phase $\phi_0$, and the number or frequency of spiral periods n.

$$\Phi = n\omega T_S + \phi_0 \tag{5}$$

Thus, since each spiral phase $\phi$ is decided beforehand by the phase $\phi_0$, the spiral period $T_S$ and the wobbler angular velocity $\omega$ at the start time point of a treatment, and hence in order to ensure the desired uniformity, a very large number of spiral loci to be overlapped are employed so that they can be regarded as statistically at random. For example, the above-mentioned first non-patent document, one or more seconds are spent so as to ensure the uniformity of the dose distribution. In this manner, the conventional spiral wobbler method involves a problem that it is necessary to perform irradiation in such a manner that a lot of spiral loci are overlapped each other.

In addition, each spiral phase $\phi$ is uniquely decided by the spiral period $T_S$ and the wobbler angular velocity $\omega$, so the wobbler angular velocity $\omega$ capable of ensuring the uniformity of the dose distribution when the spiral period $T_S$ is changed is limited, thus posing a problem that a constraint arises in the selection of the spiral period $T_S$ and the wobbler angular velocity $\omega$.

Moreover, since it is necessary to keep one continuous irradiation for one second or more, a particle beam is generally generated from a synchrotron type particle accelerator, which periodically iterates acceleration and deceleration, e.g., a periodic operation is carried out in a period of two seconds, so that the particle beam thus generated is supplied to a particle beam irradiation part at a time between the acceleration and deceleration. Thus, in order to shorten the entire irradiation time, the time to supply the particle beam is decreased as much as possible so as to operate the accelerator in an efficient manner. However, when the time to supply the particle beam is hundreds of milliseconds, the supply of the particle beam is interrupted at a time during one spiral period, thus posing a problem that there is no guarantee for which the uniformity of dose distribution in each operation period of the accelerator is ensured.

Accordingly, there is another problem that when it is intended to prevent the interruption of the supply of the particle beam during the spiral period by increasing the time to supply the particle beam, there arises a constraint in the operation period of the accelerator such as the inability to shorten the supply time of the particle beam.

Further, in a respiration synchronized operation in which the irradiation of the particle beam is turned on and off according to respiration when irradiation is performed on internal organs that are caused to move or deform in accordance with the respiration or breathing of a patient, the supply of the particle beam is interrupted during the spiral period $T_S$, thus causing a problem that there is no guarantee for which the uniformity of the dose distribution is ensured.

Furthermore, when the spiral wobbler method is applied to a layer-stacking conformal irradiation method in which irradiation on a patient is performed by dividing an exposure or irradiation area of the patient into a plurality of subareas or layers in the direction of depth thereof, a planned dose for each of the subareas or layers thus divided becomes smaller, so the number or frequency of spiral periods (hereinafter also referred to as a spiral number or frequency) is decreased, resulting in a problem that a spiral frequency required to ensure the uniformity of dose distribution can not be reached.

Besides, since the number or frequency of spiral periods is necessary to be equal to or more than a predetermined number of times, there is a further problem that when the dose rate is raised, the number or frequency of spiral periods required falls below the predetermined frequency, so the uniformity of dose distribution can not be ensured, and it is necessary to increase the exposure or irradiation time.

SUMMARY OF THE INVENTION

Accordingly, the object of the present invention is to provide a particle beam therapeutic apparatus which it is capable of ensuring the uniformity of dose distribution by overlapping the desired tracks or loci of the irradiation of a particle beam a reduced number of times.

Bearing the above object in mind, according to the present invention, there is provided a particle beam therapeutic apparatus in which a flow of a particle beam transported so as to be irradiated to a diseased part is caused to deflect in two mutually orthogonal directions perpendicular to the direction of travel of the particle beam, and the irradiation position of the particle beam is scanned, upon each period, in a manner to return to a position of irradiation located at the start of the period, whereby a plurality of loci drawn within one period are overlapped with one another thereby to irradiate a desired planned dose to the diseased part, wherein the particle beam can be interrupted only at the end of the period.

The particle beam therapeutic apparatus as constructed above according to the present invention provides the following remarkable advantageous effects. That is, irradiation is repeatedly carried out in units of the spiral period, so the possibility of irradiation being interrupted during the spiral period can be eliminated, as a result of which even if the dose rate is raised, the uniformity of dose distribution can be ensured in a reliable manner, thus making it possible to shorten the irradiation time. In addition, constraints on the operation period of an accelerator can be alleviated.

The above and other objects, features and advantages of the present invention will become more readily apparent to those skilled in the art from the following detailed description of preferred embodiments of the present invention taken in conjunction with the accompanying drawings.

BRIEF DESCRIPTION OF THE DRAWINGS

FIG. 2 is a view showing the data structure of a data table in a data storage part according to the first embodiment of the present invention.

FIG. 5 is a view showing the data structure of a data table in a data storage part of the particle beam therapeutic apparatus according to the second embodiment of the present invention.

FIG. 8 is a timing chart of signals related to a signal processing device and a turn on and off control part according to the fourth embodiment of the present invention.

FIG. 9 is a block diagram of the turn on and off control part according to the fourth embodiment of the present invention.

FIG. 11 is a view showing the data structure of a first data table in a data storage part according to the fifth embodiment of the present invention.

FIG. 12 is a view showing the data structure of a second data table in the data storage part according to the fifth embodiment of the present invention.

DESCRIPTION OF THE PREFERRED EMBODIMENTS

Hereinafter, preferred embodiments of the present invention will be described in detail while referring to the accompanying drawings.

Embodiment 1

Figure 1:
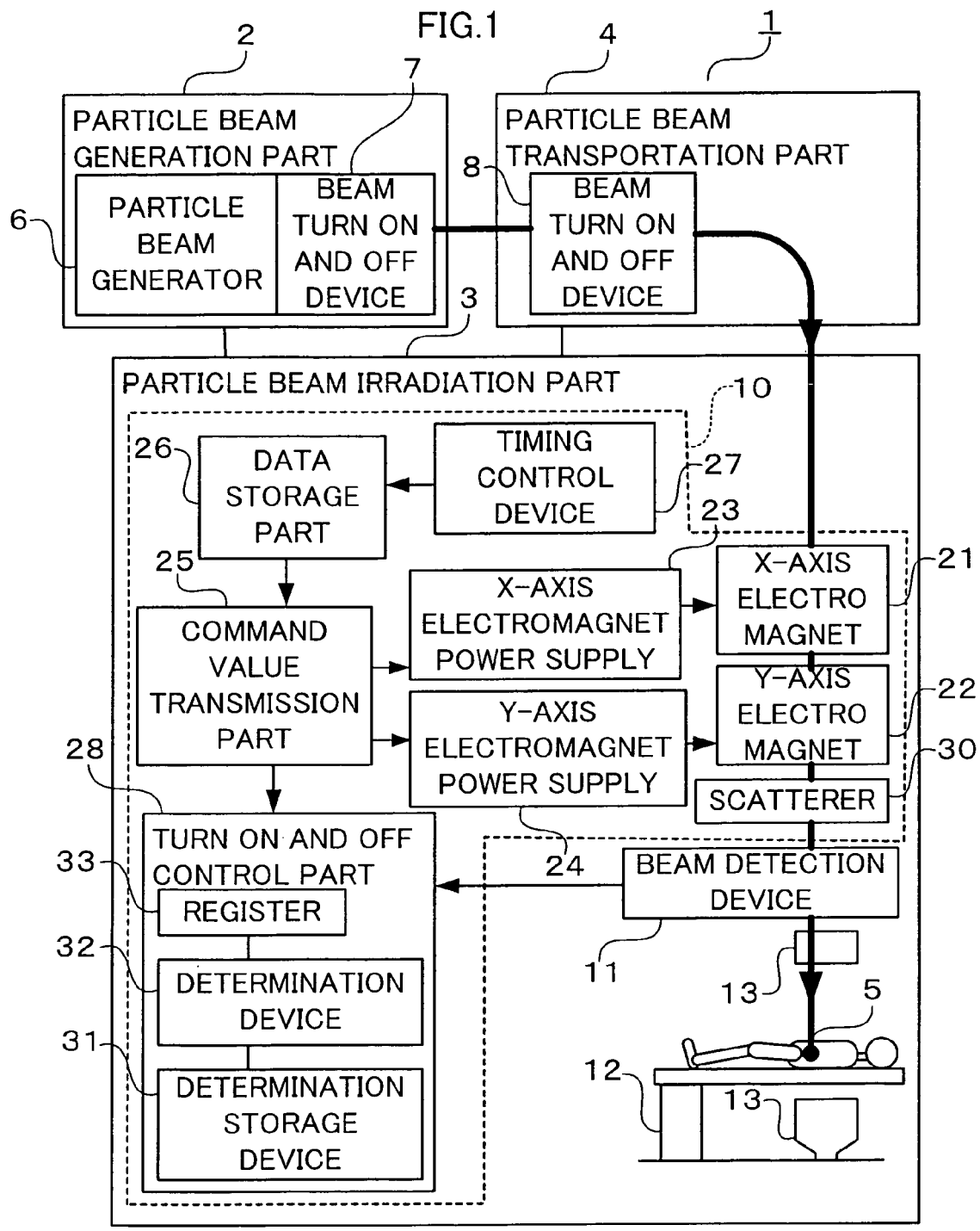
FIG. 1 is a block diagram of a particle beam therapeutic apparatus according to a first embodiment of the present invention.
Figure 3:
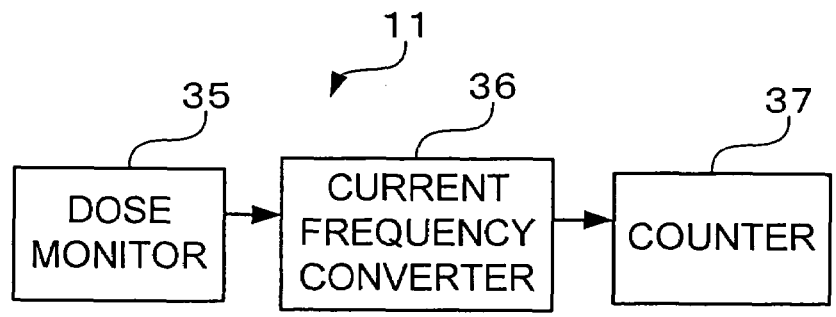
FIG. 3 is a block diagram of a beam detection device according to the first embodiment of the present invention.

FIG. 1 is a block diagram that shows a particle beam therapeutic apparatus according to a first embodiment of the present invention. FIG. 2 is a view that shows the data structure of a data table in a data storage part according to the first embodiment of the present invention, and FIG. 3 is a block diagram of a beam detection device according to the first embodiment of the present invention.

As shown in FIG. 1, the particle beam therapeutic apparatus, generally designated at reference numeral 1, according to the first embodiment of the present invention includes a particle beam generation part 2 for generating a particle beam, a particle beam irradiation part 3 for irradiating the particle beam to a target region (diseased part) 5 of a patient, and a particle beam transportation part 4 for transporting the particle beam generated by the particle beam generation part 2 to the particle beam irradiation part 3.

The particle beam generation part 2 includes a particle beam generator 6 comprised of a synchrotron type accelerator, and a beam turn on and off device 7 for controlling the turning on and off of the generated particle beam input to the particle beam transportation part 4.

In addition, the particle beam transportation part 4 includes a beam turn on and off device 8 for controlling the turning on and off of the particle beam input to the particle beam irradiation part 3.

These beam turn on and off devices 7 and 8 serve to pass the particle beam when the level of a beam turn on and off signal sent from the particle beam irradiation part 3 is "HIGH", and to interrupt the particle beam when the level of the beam turn on and off signal is "LOW".

The particle beam irradiation part 3 includes an irradiation field forming device 10 for forming an irradiation field by scanning the particle beam, a beam detection device 11 for detecting a dose to be irradiated, a patient treatment couch 12 on which a patient lies, and a patient position verification device 13 for verifying the position of the patient in the patient treatment couch 12.

The irradiation field forming device 10 includes an X-axis electromagnet 21 for deflecting the particle beam in one (hereinafter referred to as an X-axis direction) of two mutually orthogonal directions perpendicular to the direction of travel of the particle beam, a Y-axis electromagnet 22 for deflecting the particle beam in a direction (hereinafter referred to as a Y-axis direction) perpendicular to the X-axis direction orthogonal to the direction of travel of the particle beam, an X-axis electromagnet power supply 23 for supplying an X-axis exciting current to the X-axis electromagnet 21 to excite or magnetize it, a Y-axis electromagnet power supply 24 for supplying a Y-axis exciting current to the Y-axis electromagnet 22 to excite or magnetize it, a command value transmission part 25 for sending an X-axis exciting current command value and a Y-axis exciting current command value to the X-axis electromagnet power supply 23 and the Y-axis electromagnet power supply 24, respectively, a data storage part 26 for storing a pair of X-axis exciting current designated value and Y-axis exciting current designated value and data indicating an end of a spiral period for each consecutive address, a timing control device 27 for generating timing at which the X-axis exciting current command value and the Y-axis exciting current command value are read from the data storage part 26, a turn on and off control part 28 for monitoring the exposure or irradiation dose, determining the request of the particle beam, and controlling the beam turn on and off devices 7, 8, and a scatterer 30 for scattering the particle beam of a small diameter into a predetermined diameter.

In the X-axis electromagnet 21, the flow of the particle beam is deflected into the X-axis direction by supplying the X-axis exciting current to an unillustrated excitation coil while changing the magnitude and direction thereof. Similarly, in the Y-axis electromagnet 22, the flow of the particle beam is deflected into the Y-axis direction by supplying the Y-axis exciting current to an unillustrated excitation coil while changing the magnitude and direction thereof.

The X-axis electromagnet power supply 23 supplies the X-axis exciting current to the X-axis electromagnet 21 based on the X-axis exciting current command value input thereto, and and the Y-axis electromagnet power supply 24 supplies the Y-axis exciting current to the Y-axis electromagnet 22 based on the Y-axis exciting current command value input thereto.

The data storage part 26 is provided with a data table having a data structure, as shown in FIG. 2. in the data table, three data areas and one pointer region are set for each three consecutive addresses, respectively, and an X-axis exciting current designated value and a Y-axis exciting current designated value for each address are stored in two data areas, respectively. Also, the remaining one data area is called a spiral period end bit, in which data indicating the end or termination of a spiral period is stored, and "1" is stored therein at the address of the end or termination of the spiral period, whereas "0" is stored therein at other addresses.

In addition, "1" is stored in a pointer area corresponding to an address incremented based on a clock signal, whereas "0" is stored in pointer areas corresponding to the other addresses. The data in a data area at an address whose pointer area has "1" stored therein is sent to the command value transmission part 25.

The X-axis exciting current designated value and the Y-axis exciting current designated value are calculated based on the following expressions (6) through (9) at each predetermined clock period W that equally divides the spiral period $T_S$ into m parts, and stored in the data storage part 26. For example, if the spiral period $T_S$ is equally divided by 40 milliseconds into 200 parts, the clock period W becomes 0.2 milliseconds, and 200 addresses are occupied in one spiral period $T_S$. In this case, assuming that the addresses are from the 0th to 199th address, "1" is stored in a spiral period end bit at the 199th address, and predetermined data for a number or frequency of spiral periods of 200 is stored in the data storage part 26.

$$I_X = A\sqrt{\frac{2(Wi - nT_S)}{T_S}} \sin(\omega Wi + \phi_0) \quad (6)$$

where $n\frac{T_S}{W} \leq i < (n + 0.5)\frac{T_S}{W}$ $$I_X = A\sqrt{\frac{2\{(n+1)T_S - Wi\}}{T_S}} \sin(\omega Wi + \phi_0) \quad (7)$$

where $(n + 0.5)\frac{T_S}{W} \leq i < (n + 1)\frac{T_S}{W}$ $$I_Y = A\sqrt{\frac{2(Wi - nT_S)}{T_S}} \cos(\omega Wi + \phi_0) \quad (8)$$

where $n\frac{T_S}{W} \leq i < (n + 0.5)\frac{T_S}{W}$ $$I_Y = A\sqrt{\frac{2\{(n+1)T_S - Wi\}}{T_S}} \cos(\omega Wi + \phi_0) \quad (9)$$

where $(n + 0.5)\frac{T_S}{W} \leq i < (n + 1)\frac{T_S}{W}$

In the data storage part 26, the address is incremented each time a clock signal is input thereto, and the data of an X-axis exciting current designated value, a Y-axis exciting current designated value and a spiral period end bit stored at that address are read and sent to the command value transmission part 25.

The command value transmission part 25 sends an X-axis exciting current command value to the X-axis electromagnet power supply 23, and a Y-axis exciting current command value to the Y-axis electromagnet power supply 24 based on the X-axis exciting current designated value and the Y-axis exciting current designated value, respectively, sent from the data storage part 26. Further, when the data of the spiral period end bit is determined as "1" based on the data of the spiral period end bit sent from the data storage part 26, the command value transmission part 25 sends a pulse, which sequentially changes into a "LOW", a "HIGH" and a "LOW" level, to the turn on and off control part 28 as a spiral period end signal.

The timing control device 27 inputs a clock signal of a clock period W obtained from the spiral period $T_S$ and the number of equal divisions m thereof, and a reset signal to restore the address of the data storage part 26 to the first address to the data storage part 26.

The turn on and off control part 28 includes a determination storage device 31 in which a planned dose set prior to a treatment by particle beam irradiation is stored, a determination device 32 that compares the exposure dose from the beam detection device 11 and the planned dose, determines the presence or absence of a beam request, and changes the level of a beam request signal, and a register 33 that sends the level of the beam request signal to the beam turn on and off devices 7, 8 at each breakpoint or end of the spiral period as a beam turn on and off signal. The beam request signal is at a "HIGH" level in the presence of a beam request, and at a "LOW" level in the absence of a beam request.

As shown in FIG. 3, the beam detection device 11 includes a dose monitor 35 for measuring the flow of an electric charge of the particle beam irradiated, i.e., a beam current, a current frequency converter 36 for converting the beam current into a pulse train of a frequency proportional to the magnitude of the beam current, and a counter 37 for counting the number of pulses contained in the pulse train to obtain a cumulative count value at a predetermined time limit. This count value represents an exposure dose.

At the time of starting a treatment, the exposure dose is zero and is less than the planned dose, so the level of the beam request signal becomes "HIGH". When an unillustrated switch for starting irradiation is turned on, a clock signal is sent to the data storage part 26, and the address of the data storage part 26 is incremented each time the clock signal is input thereto, and the data of an X-axis exciting current designated value, a Y-axis exciting current designated value and a spiral period end bit stored at that address are read out so that the X-axis exciting current command value and the Y-axis exciting current command value thus read out are sent to the X-axis electromagnet power supply 23 and the Y-axis electromagnet power supply 24, respectively. The X-axis electromagnet power supply 23 and the Y-axis electromagnet power supply 24 act to excite the X-axis electromagnet 21 and the Y-axis electromagnet 22, respectively, thereby effect the flow of the particle beam.

The increment of the address is repeated, and when the last address of the spiral period is reached, the data of the spiral period end bit read out at this time is "1", so a pulse in the form of a spiral period end signal is sent out.

Since the irradiation dose in one spiral period does not reach the planned dose and the level of the beam request signal remains "HIGH", the particle beam is supplied as it is, and irradiation in the following spiral period is continued.

By repeating irradiation in a plurality of spiral periods, irradiation in the final spiral period in which the exposure dose reaches the planned dose starts. When the exposure dose reaches the planned dose at a certain address after starting from the first address in this final spiral period, the level of the beam request signal changes into a "LOW" level. However, since a pulse in the form of a spiral period end signal has not yet input to the register 33, the level of the beam turn on and off signal remains "HIGH", and when the address at the end or termination of this spiral period is reached, the spiral period end bit is "1", so a pulse in the form of a spiral period end signal is sent to the register 33.

When the pulse is input to the register 33, the level of the beam turn on and off signal changes into a "LOW" level, and the particle beam is interrupted.

Since irradiation is repeatedly carried out in units of the spiral period in this manner, the possibility of irradiation being interrupted during the spiral period can be eliminated, so even if the dose rate is raised, the uniformity of dose distribution can be ensured in a reliable manner, thus making it possible to shorten the irradiation time. Additionally, constraints on the operation period of an accelerator can be alleviated.

Here, note that since irradiation is turned on and off at each spiral period, the control of the exposure dose is carried out in units of the exposure dose irradiated in one spiral period, so the dose actually irradiated will always exceed the planned dose.

For example, assuming that the operation period of the accelerator is 2 seconds, the beam turn-on time is 400 milliseconds, and the average dose rate irradiated by the accelerator is 2 Gy/minute, it takes 60 seconds to irradiate a planned dose of 2 Gy onto a diseased part, and hence 30 operations of the accelerator are needed. For 30 operations as a whole, the beam turn-on time becomes 12 seconds, and the exposure dose in a spiral period of 43.5 milliseconds becomes 0.00725 Gy. The exposure doses from the first time to the 29th time in the 30 operations are accumulated or added up to one another, and when the total sum of the exposure doses thus obtained does not reach the planned dose, a shift is made to irradiation in the following (30th) spiral period. Thus, the amount of dose exceeding the planned dose is an exposure dose for one spiral period at the maximum, and hence the accuracy of the exposure dose with respect to the planned dose can be ensured to a satisfactory extent, for instance with 0.36% in the above-mentioned example.

In addition, although a method of performing scanning in a continuous manner while continuing irradiation, a method of starting irradiation of a beam after the beam has been moved with the irradiation of the beam being once stopped temporarily, a method of repeating the movement and stoppage of a beam while continuing irradiation, etc., are known as beam irradiation according to a spiral wobbler method, either of these methods can be applied to the particle beam therapeutic apparatus 1 of the present invention.

Embodiment 2

Figure 4:
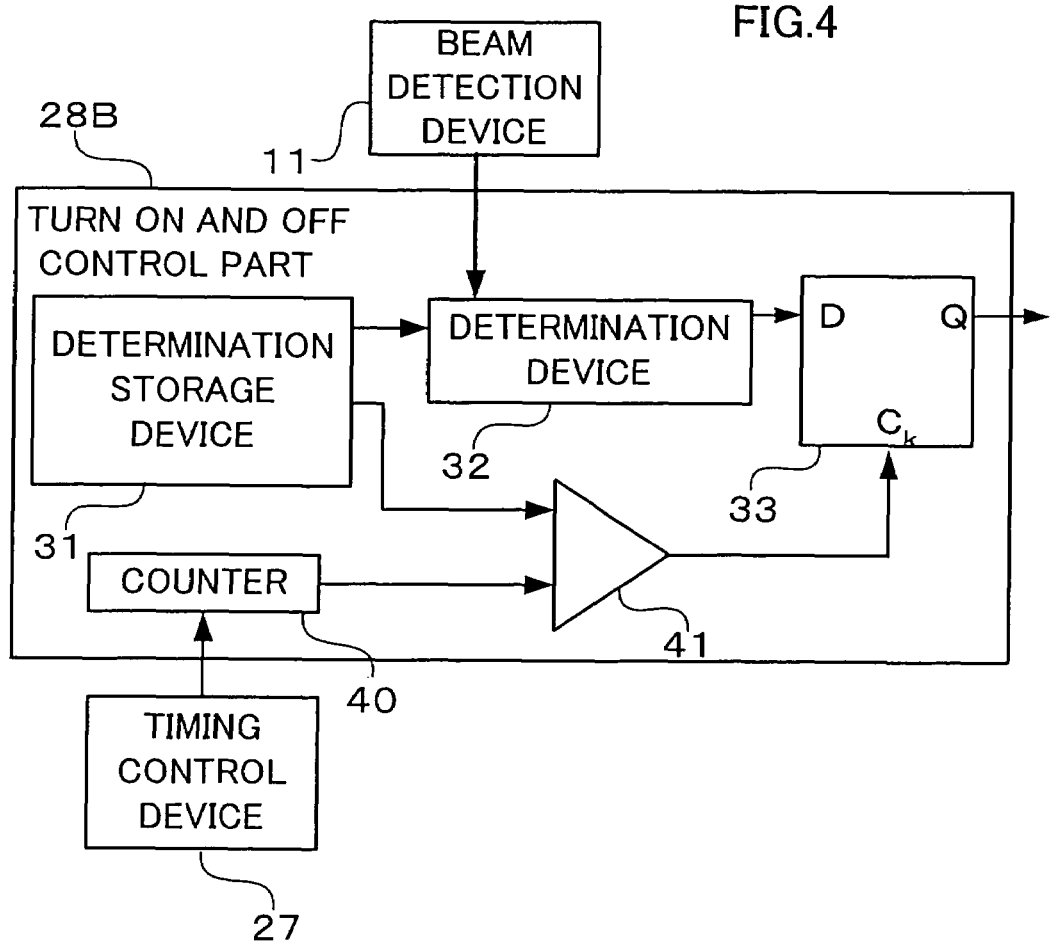
FIG. 4 is a block diagram of a turn on and off control part of a particle beam therapeutic apparatus according to a second embodiment of the present invention.

FIG. 4 is a block diagram of a turn on and off control part in a particle beam therapeutic apparatus according to a second embodiment of the present invention. FIG. 5 shows the data structure of a data table in the data storage part of the particle beam therapeutic apparatus according to the second embodiment of the present invention. In the above-mentioned first embodiment, the particle beam is turned on and off by reading a spiral period end bit stored in the data storage part 26 and inputting a pulse in the form of a spiral period end signal to the register 33, but in the second embodiment, the clock signal from the timing control device 27 is counted, and the count value thus obtained is compared with the number of divisions of the spiral period stored beforehand in the determination storage device 31, so that when the count value becomes equal to the number of divisions of the spiral period, the beam is turned on and off by sending a pulse in the form of a spiral period end signal to the register 33. In this regard, as shown in FIG. 5, the spiral period end bits as used in the first embodiment are omitted from the data table of the data storage part 26 unlike the first embodiment, but the other construction of this embodiment is similar to the first embodiment, and hence like components or parts are identified by like symbols while omitting a detailed explanation thereof.

As shown in FIG. 4, a turn on and off control part 28B according to this second embodiment includes a counter 40 for counting a clock signal from the timing control device 27 to obtain a count value, and a comparison circuit 41 for comparing the count value with the number of divisions of a spiral period stored beforehand in the determination storage device 31 so as to send a pulse in the form of a spiral period end signal to the register 33 in accordance with the result of the comparison. In the counter 40, the count value is reset to start a new count when the pulse of in the form of the spiral period end signal is sent from the comparison circuit 41.

Since such a particle beam therapeutic apparatus according to the second embodiment can detect the end or termination of a spiral period by counting the clock signal with the counter 40, the data related to the end or termination of the spiral period need not be separately stored in the data storage part 26.

Embodiment 3

Figure 6:
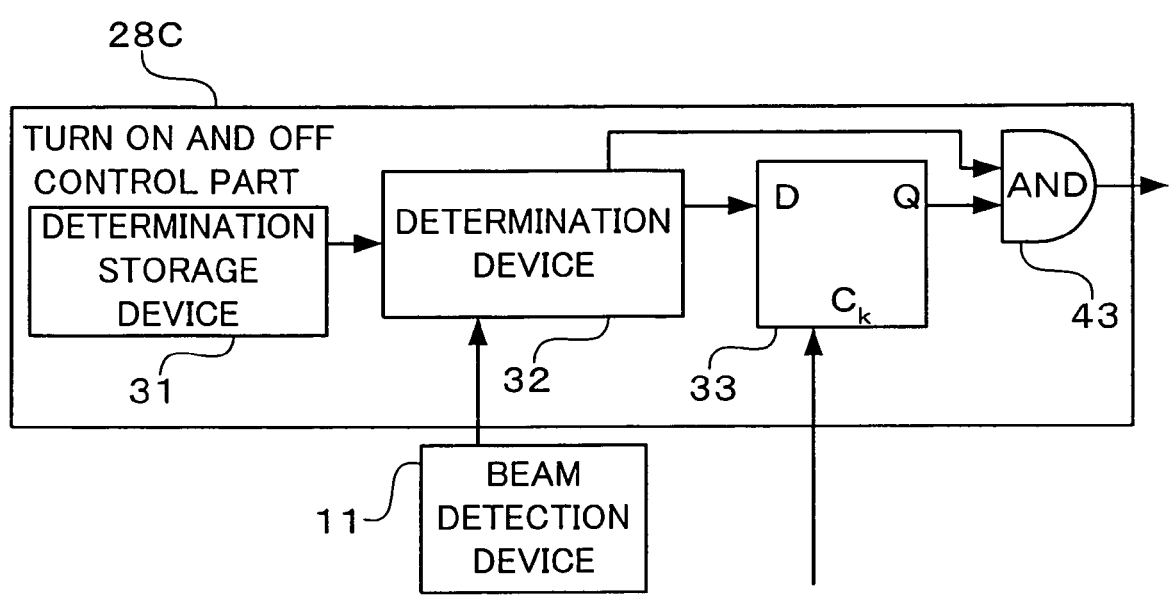
FIG. 6 is a block diagram of a turn on and off control part of a particle beam therapeutic apparatus according to a third embodiment of the present invention.

FIG. 6 is a block diagram of a turn on and off control part in a particle beam therapeutic apparatus according to a third embodiment of the present invention. The turn on and off control part 28C according to this third embodiment is different from the turn on and off control part 28 of the above-mentioned first embodiment in the addition of an immediate beam interruption function, but the other construction of this third embodiment is similar to the first embodiment, and hence like components or parts are identified by like symbols while omitting a detailed explanation thereof. In the turn on and off control part 28C according to the third embodiment, as shown in FIG. 6, an immediate beam interruption signal, which becomes a "LOW" level when the exposure dose from the determination device 32 reaches the planned dose and a "HIGH" level at the other times, is input to an AND circuit 43.

Also, the immediate beam interruption signal and a Q output of the register 33 are input to the AND circuit 43, which in turn outputs a beam turn on and off signal. The level of the beam turn on and off signal is changed into "LOW" when at least either one of the immediate beam interruption signal and the Q output of the register 33 is "LOW". Thus, the irradiation of the beam can be interrupted even during a spiral period if necessary.

This immediate beam interruption signal can also be created by turning on an unillustrated interruption switch.

In such a particle beam therapeutic apparatus as constructed above, the uniformity of dose distribution is not deteriorated even if the irradiation is interrupted during a spiral period at the time when the number or frequency of spiral periods to ensure the uniformity of dose distribution exceeds a required value. As a result, it is possible to reduce the amount of dose exceeding the planned dose by interrupting the irradiation immediately when the planned dose has been completed or reached.

In addition, the immediate beam interruption signal can be used as an emergency stop signal, so an irradiation stop time (i.e., the time required to stop irradiation) can be shortened upon occurrence of abnormality such as cough, sudden motion of a patient, etc., thus making it possible to improve safety.

Embodiment 4

Figure 7:
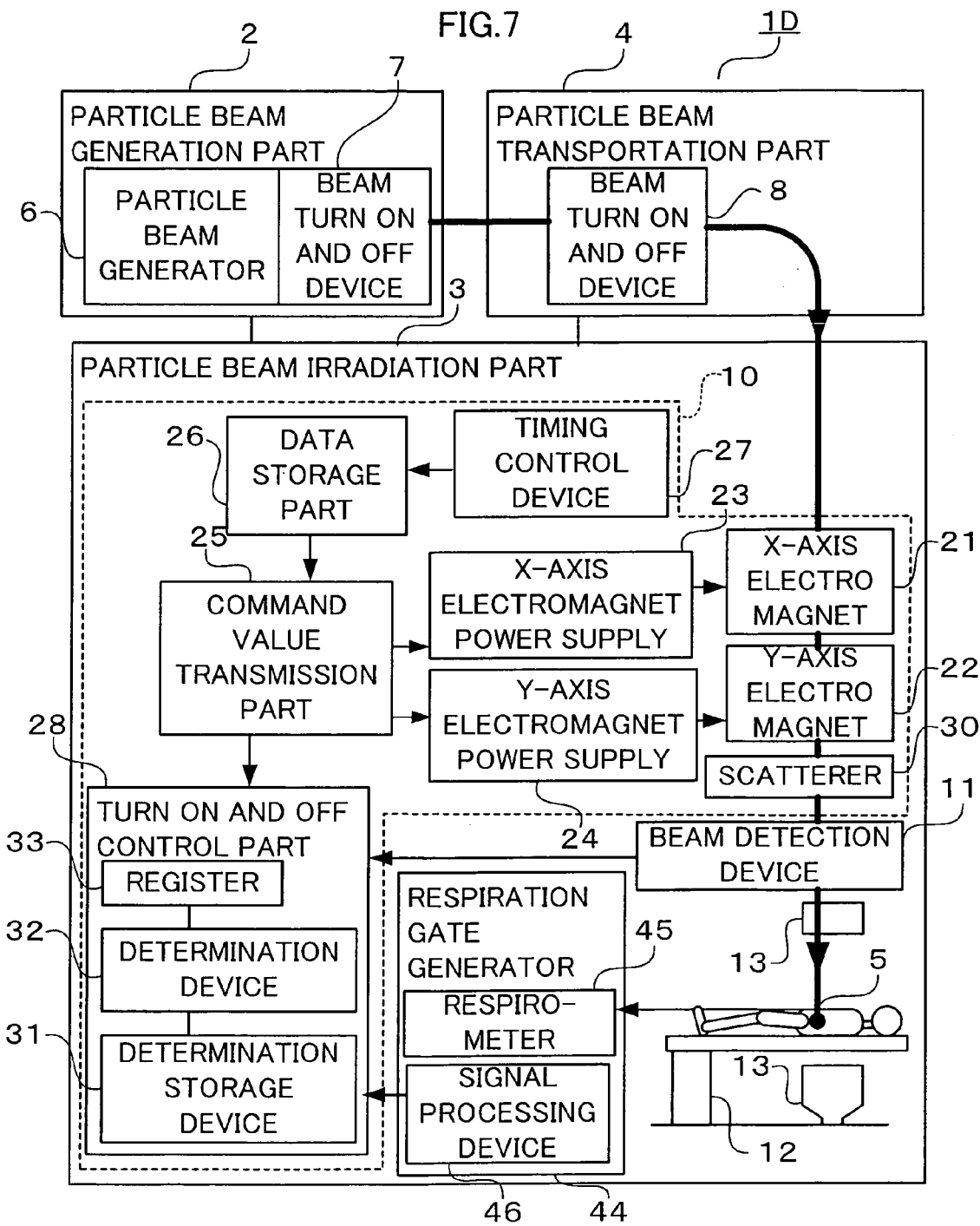
FIG. 7 is a block diagram of a particle beam therapeutic apparatus according to a fourth embodiment of the present invention.

FIG. 7 is a block diagram of a particle beam therapeutic apparatus according to a fourth embodiment of the present invention. FIG. 8 is a timing chart of signals related to a signal processing device and a turn on and off control part according to the fourth embodiment of the present invention.

FIG. 9 is a block diagram of the turn on and off control part according to the fourth embodiment of the present invention. The particle beam therapeutic apparatus 1D according to the fourth embodiment includes a respiration gate generator 44 in the form of a patient monitoring device which is added to the above-mentioned particle beam therapeutic apparatus 1 according to the first embodiment of the present invention, and the apparatus 1D is further different from the apparatus 1 in a turn on and off control part 28D which is changed from the corresponding turn on and off control part 28 in relation to the addition of the respiration gate generator 44, but the other construction of this fourth embodiment is similar to the first embodiment, and hence like components or parts are identified by like symbols while omitting a detailed explanation thereof. The respiration gate generator 44 according to the fourth embodiment includes a respirometer 45 for measuring the respiration of a patient, and a signal processing device 46 for processing a signal based on the patient's respiration thus measured, as shown in FIG. 7. For example, a product AZ773 made by Anzai Medical Co., Ltd., is known as the respiration gate generator 44, but there are a variety of methods other than this and hence the present invention is not limited to the use of the method as described herein.

In the respirometer 45, the respiratory state of a patient 5 is continuously measured, and in the signal processing device 46, a pneumogram is created based on the number or frequency of respirations thus measured, as shown in FIG. 8. Then, when the pneumogram is below the threshold as a result of the comparison of the pneumogram with a preset threshold, it is determined that the respiration is stable, and the level of the respiration gate signal is changed to "HIGH", whereas when the pneumogram is above the threshold, it is determined that the respiration is unstable, and the level of the respiration gate signal is changed to "LOW".

The turn on and off control part 28D according to the fourth embodiment includes an AND circuit 47 that is arranged between a determination device 32 and a register 33, as shown in FIG. 9, for outputting a beam gate signal based on a beam request signal and a respiration gate signal input thereto. When the beam request signal and the respiration gate signal are both at a "HIGH" level, the level of the beam gate signal becomes "HIGH".

The beam gate signal and a pulse in the form of a spiral period end signal are input to the register 33, which then outputs a beam turn on and off signal. When the pulse in the form of the spiral period end signal is sent from the command value transmission part 25, i.e., when the spiral period ends, the level of a D input terminal of the register 33 is reflected on the level of a Q output terminal thereof. As a result, only when the level of the beam request signal is "HIGH" and when the level of the respiration gate signal is also "HIGH", the beam turn on and off signal becomes "HIGH", so a particle beam is supplied to the particle beam irradiation part 3.

In this manner, the irradiation of the particle beam can be performed only when the patient's respiration is stable. Here, not that when the spiral period $T_S$ is set to 43.478 milliseconds, the period of respiration is generally about 2 seconds to 6 seconds, so if the time required for interrupting the particle beam in respiration synchronization is set to 0.1 seconds or less, it is possible to follow a change in the respiratory state to a satisfactory extent. Since in the first embodiment, the particle beam is turned on and off in units of the spiral period irrespective of the patient's respiration, so the uniformity of dose distribution can be ensured to a satisfactory extent, but it is also possible to advance the management of the uniformity of dose distribution in an easy manner even in the case of the respiration synchronized operation as in the fourth embodiment.

Embodiment 5

Figure 10:
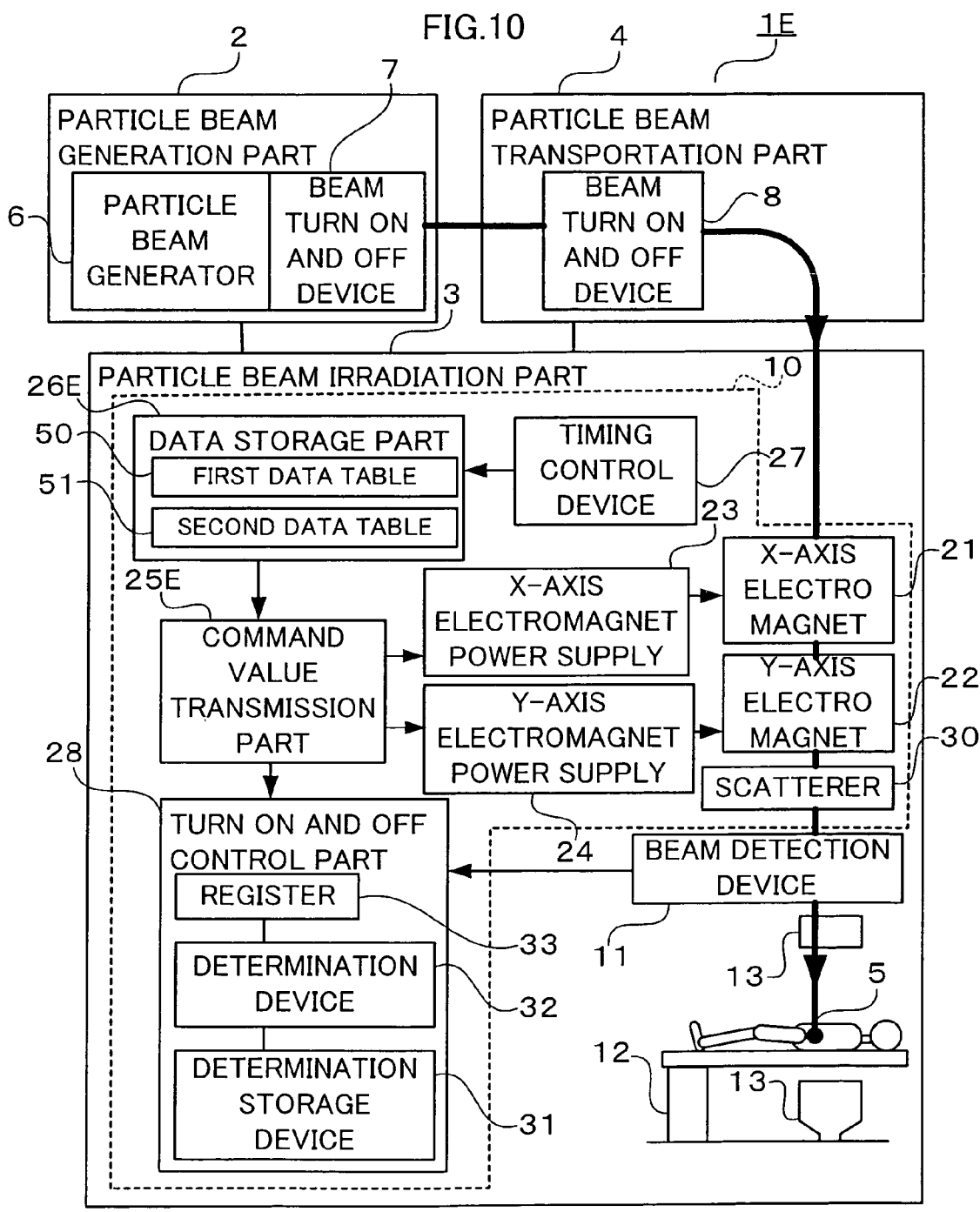
FIG. 10 is a block diagram of a particle beam therapeutic apparatus according to a fifth embodiment of the present invention.
Figure 13:
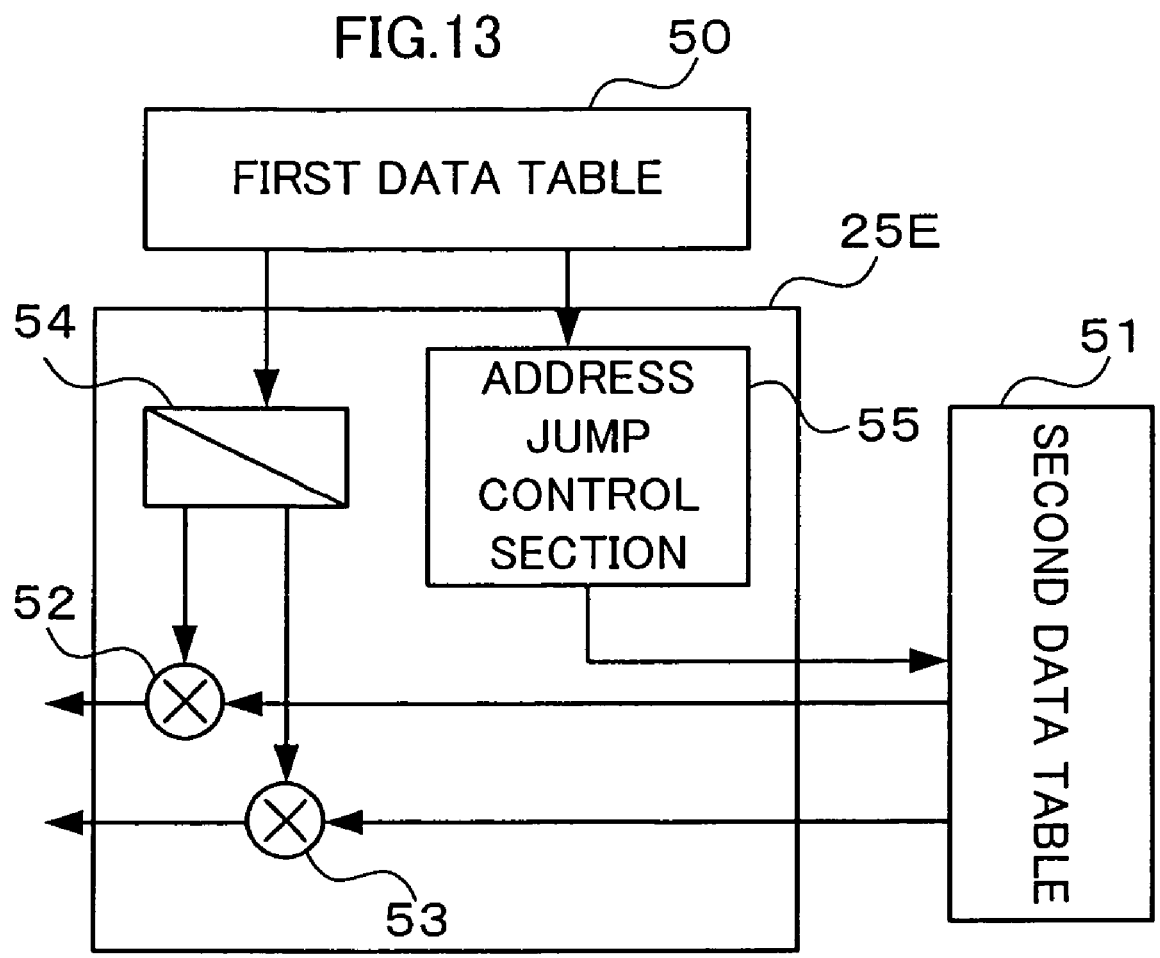
FIG. 13 is a block diagram of a command value transmission part according to the fifth embodiment of the present invention.
Figure 14:
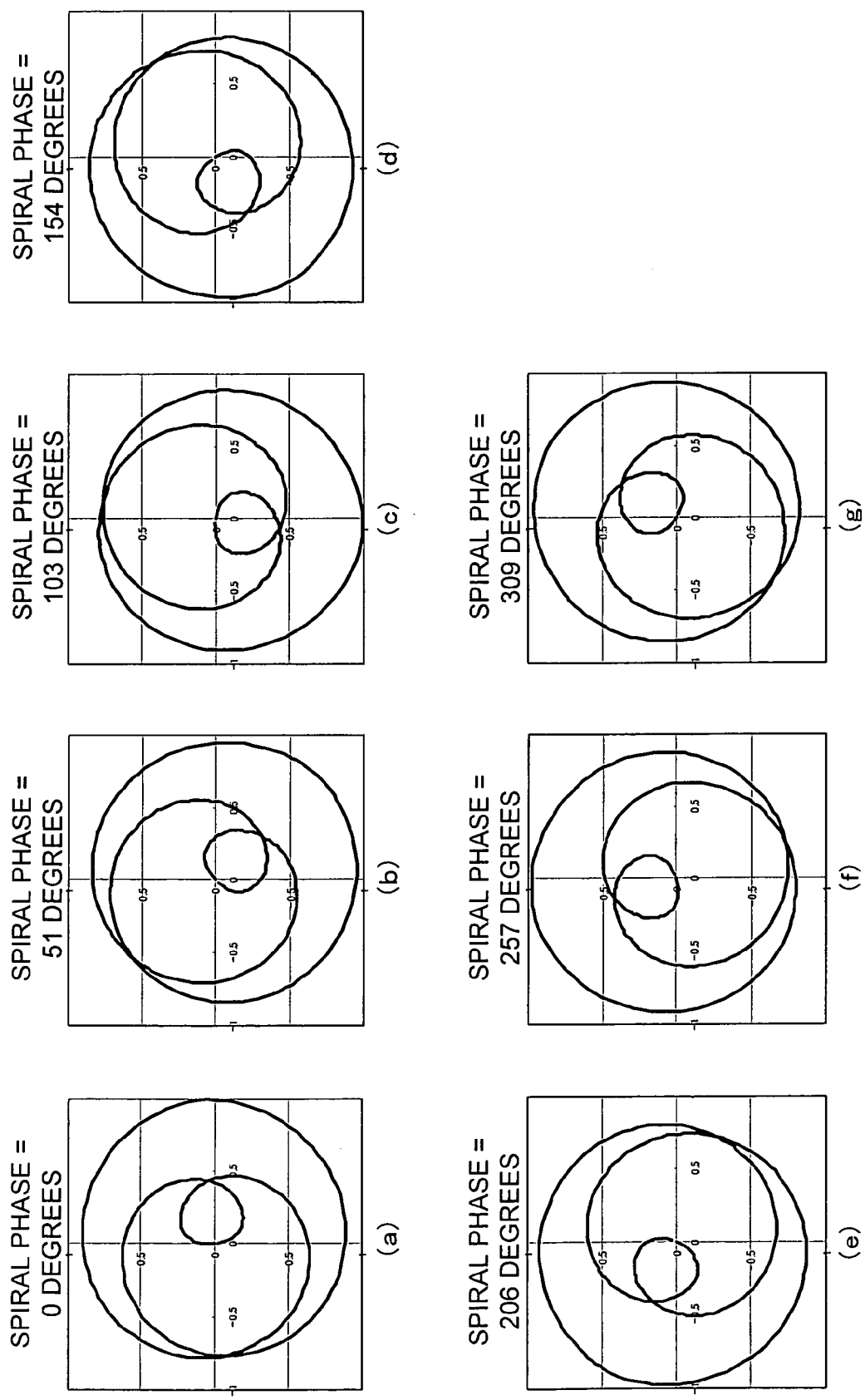
FIG. 14 is a view showing a spiral locus scanned by the particle beam therapeutic apparatus according to the fifth embodiment of the present invention.

FIG. 10 is a block diagram of a particle beam therapeutic apparatus according to a fifth embodiment of the present invention. FIG. 11 is a view showing the data structure of a first data table in a data storage part according to the fifth embodiment of the present invention. FIG. 12 is a view showing the data structure of a second data table in the data storage part according to the fifth embodiment of the present invention. FIG. 13 is a block diagram of a command value transmission part according to the fifth embodiment of the present invention. FIG. 14 is a view showing a spiral locus scanned by the particle beam therapeutic apparatus according to the fifth embodiment of the present invention. As shown in FIG. 10, the particle beam therapeutic apparatus 1E according to the fifth embodiment is different from the particle beam therapeutic apparatus 1 according to the first embodiment in a command value transmission part 25E and a data storage part 26E, but the other construction of this embodiment is similar to the first embodiment, and hence like components or parts are identified by like symbols while omitting a detailed explanation thereof.

Two data tables 50, 51 are set in the data storage part 26E according to the fifth embodiment. The first data table 50 has two data areas and one pointer area that are set with respect to each of the addresses of sequential numbers, as shown in FIG. 11. Data of an amplitude B is stored in one data area for each address, and data, which is called a spiral period end bit and represents the end of a spiral period, is stored in the remaining one data area. The value "1" is stored when the address is the end of the spiral period, whereas the value "0" is stored otherwise.

In addition, the data to indicate the currently designated address in the addresses designated sequentially based on the clock signal is stored in one pointer area, in which "1" is stored, whereas "0" is stored in the pointer areas at the other addresses.

The amplitude B is obtained from the spiral period $T_S$ and the clock period W based on the following expressions (10) and (11).

$$B = A\sqrt{\frac{2Wi}{T_S}} \quad (10)$$

where $0 \leq i < 0.5\frac{T_S}{W}$ $$B = A\sqrt{\frac{2(T_S - Wi)}{T_S}} \quad (11)$$

where $0.5\frac{T_S}{W} \leq i < \frac{T_S}{W}$ where i is the count value of the clock period which is a positive integer.

The first data table 51 also has one data area and two pointer areas (i.e., an X pointer area and a Y pointer area) that are set with respect to each of the addresses of sequential numbers, as shown in FIG. 12. Data of a sine wave function S is stored in the one data area, and the data to indicate the currently designated addresses in two addresses designated sequentially based on the clock signal are stored in the two pointer areas, in which "1" is stored, whereas "0" is stored in the pointer areas at the other addresses. These two pointer areas move in association with each other in such a manner that the corresponding sine wave functions S are 90 degrees out of phase from each other. Here, a Y pointer advances 90 degrees from an X pointer.

A sine wave function S is obtained from the wobbler angular velocity ω and the clock period W based on the following expression (12).

$$S=\sin(\omega Wi) \quad (12)$$

The command value transmission part 25E includes, as shown in FIG. 13, a distributor 54 that distributes an amplitude B read from the first data table 50 to two multipliers 52 and 53 in synchronization with the clock signal, a address jump control part 55 that makes an address of the second data table 51 corresponding to an amount αφ of phase change obtained based on the following expression (13) jump when the data of the spiral period end bit read from the first data table 50 is "1", an X-axis multiplier 52 that calculates an X-axis exciting current command value by multiplying the amplitude B and a sine wave function S at an address indicated by an X pointer of the second data table 51 and sends it to an X-axis electromagnet power supply 23, and a Y-axis multiplier 53 that calculates a Y-axis exciting current command value by multiplying the amplitude B and a sine wave function S at an address indicated by a Y pointer of the second data table 51 and sends it to a Y-axis electromagnet power supply 24. Here, $T_W$ represents the wobbler period.

$$\Delta\phi = \text{mod}(T_W, T_S) \div T_W \times 360 \quad (13)$$

For example, assuming that the clock period W is 0.194 milliseconds and the wobbler frequency is 57 Hz, i.e., the wobbler period $T_W$ is 17 milliseconds, the phase at the spiral period start time point can be made a fraction of 360 degrees. Specifically, the spiral phase can be adjusted to 0 degrees, 51 degrees, 103 degrees, 154 degrees, 206 degrees, 257 degrees, and 309 degrees, respectively, by using one seventh of 360 degrees as the unit of measurement. Also, the phase can be adjusted to 0 degrees, 154 degrees, 309 degrees, 103 degrees, 257 degrees, 51 degrees, and 206 degrees, respectively, by using three sevenths of 360 degrees as the unit of measurement. In order to advance the phase by 51 degrees, it is necessary to advance the address by (17.54 milliseconds÷0.194 milliseconds×51 degrees÷360 degrees=12.808), i.e., approximately 13. When a spiral period end bit of "1" is received, it needs only to resume reading the sine wave function S from the address obtained by adding 13 to the current address of the second data table 51.

The spiral tracks or loci starting from the spiral phases of 0 degrees, 51 degrees, 103 degrees, 154 degrees, 206 degrees, 257 degrees, and 309 degrees, respectively, are shown in FIG. 14. Thus, the spiral loci can be uniformly distributed by setting appropriate phases.

The data of the amplitude B for one spiral period has only to be stored in the first data table 50, and the data of the sine wave function S for one wobbler period also has only to be stored in the second data table 51, so it needs only to provide the data storage part 26E of a small capacity. In each of the data tables 50, 51, when the current address thereof reaches the final end, it is controlled to automatically return to the first address.

Here, note that in case where the end of the address is reached when the address jumps by a designated value, a predetermined address has only to be jumped to while continuously counting the address from the first address.

In such a particle beam therapeutic apparatus 1E, the data of the amplitude B and the data of the sine wave function S are stored in the first data table 50 and the second data table 51, respectively, while being separated from each other, so only respective data of the amplitude and the function for one period need to be stored, preparation for the data becomes easy, and the required storage capacity also becomes small.

In addition, since a predetermined value for which the address is to be jumped so as to make dose distribution uniform can be obtained beforehand, the uniformity of dose distribution can be ensured only by overlapping small amounts of the spiral loci with each other. As a result, it is possible to carry out irradiation at an increased dose rate.

Moreover, when the wobbler period $T_W$ and the spiral period $T_S$ are to be changed, the amount of jump of the address capable of ensuring the uniformity of dose distribution can be obtained beforehand, so constraints on the selection of the wobbler period $T_W$ and the spiral period $T_S$ can be decreased.

Further, it is also possible to perform the operation of the accelerator with improved efficiency by shortening the operation period of the accelerator.

Embodiment 6

Figures 15, 16:
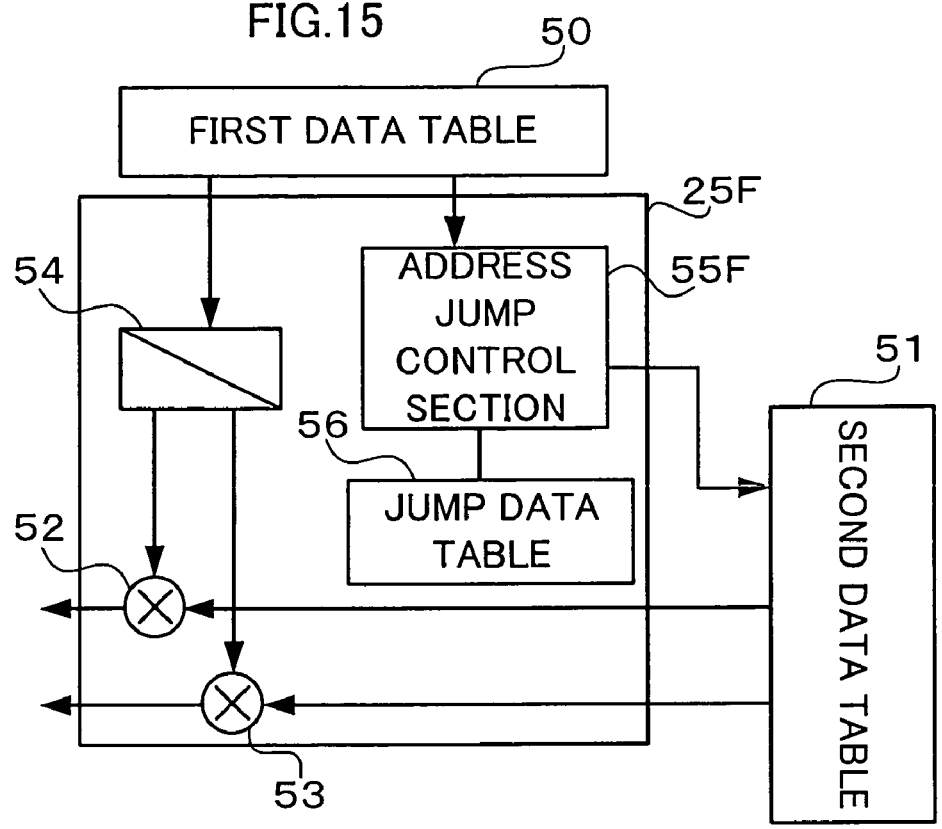
FIG. 15 is a block diagram of a command value transmission part of a particle beam therapeutic apparatus according to a sixth embodiment of the present invention.
FIG. 16 is a view showing the data structure of a jump data table according to the sixth embodiment of the present invention.

FIG. 15 is a block diagram of a command value transmission part of a particle beam therapeutic apparatus according to a sixth embodiment of the present invention. FIG. 16 is a view that shows the data structure of a jump data table according to the sixth embodiment of the present invention. The particle beam therapeutic apparatus according to the sixth embodiment is different from the above-mentioned particle beam therapeutic apparatus according to the fifth embodiment in a command value transmission part 25F, but the other construction of this embodiment is similar to the fifth embodiment, and hence like components or parts are identified by like symbols while omitting a detailed explanation thereof. As shown in FIG. 15, the command value transmission part 25F according to the sixth embodiment is different from the command value transmission part 25E according to the fifth embodiment in an address jump control section 55F and a jump data table 56 newly added in association therewith, but the other construction of the command value transmission part 25F of this embodiment is similar to the one 25E of the fifth embodiment, and hence like components or parts are identified by like symbols while omitting a detailed explanation thereof.

When the read data of the spiral period end bit of the first data table 50 is "1", the address jump control section 55F according to the sixth embodiment increments the address of the jump data table 56, reads an X-axis address and a Y-axis address indicating the jump destination of the incremented address, and sets "1" to the X pointer and the Y pointer of the second data table 51, respectively, corresponding to these addresses. Then, the data of the sine wave function S at the address where "1" is set to its X pointer is output to the X-axis multiplier 52 and the data of the sine wave function S at the address where "1" is set to its Y pointer is output to the Y-axis multiplier 53. Thereafter, the operation of this sixth embodiment is similar to the corresponding operation of the fifth embodiment as described above.

The jump data table 56 has two data areas and one pointer area that are set with respect to each of the addresses of sequential numbers, as shown in FIG. 16. Two, X-axis address and Y-axis address are stored in the two data areas, respectively, and these X-axis address and Y-axis address indicate an address of the second data table 51. The data of the sine wave function S at the Y-axis address of the second data table 51 is a value that advances 90 degrees from the data of the sine wave function S at the X-axis address of the second data table 51.

The address related to the spiral phase of the current spiral period is designated in one pointer area, and when the value of the spiral period end bit is "1", the address is incremented by one and the pointer area moves in conjunction therewith.

Such a particle beam therapeutic apparatus can control the spiral phase at each spiral period, so if the combination of the most efficient spiral phase combination is decided beforehand to form the irradiation field of a dose distribution uniformly, the planned dose can be irradiated by irradiating small the number or frequency of spiral periods while maintaining uniformity.

Moreover, the spiral phase can be arbitrarily set while changing the amount of jump, so it is possible to achieve optimal overlapping of spiral tracks or loci.

Embodiment 7

Figure 17:
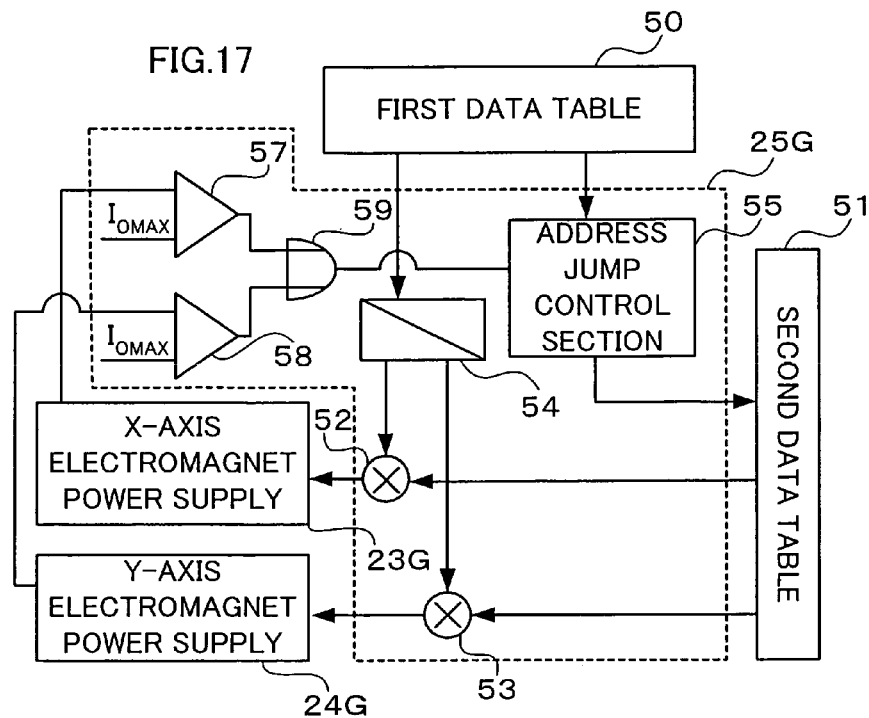
FIG. 17 is a view showing a command value transmission part of a particle beam therapeutic apparatus according to a seventh embodiment of the present invention.

FIG. 17 is a view that shows a command value transmission part of a particle beam therapeutic apparatus according to a seventh embodiment of the present invention. The particle beam therapeutic apparatus according to the seventh embodiment is different from the above-mentioned particle beam therapeutic apparatus 1E according to the fifth embodiment in the addition of a function to monitor an excitation current, but the other construction of this seventh embodiment is similar to the fifth embodiment, and hence like components or parts are identified by like symbols while omitting a detailed explanation thereof. An X-axis electromagnet power supply 23G and a Y-axis electromagnet power supply 24G according to the seventh embodiment are each provided at their output with an unillustrated ammeter for measuring an excitation current value.

In addition, as shown in FIG. 17, the command value transmission part 25G according to the seventh embodiment is different from the command value transmission part 25E of the fifth embodiment, in the addition of an X-axis comparator 57 that generates an X-axis overcurrent signal when an X-axis exciting current value input from an unillustrated ammeter is greater than a preset threshold $O_{OMAX}$, a Y-axis comparator 58 that generates a Y-axis overcurrent signal when a Y-axis exciting current value input from an unillustrated ammeter is greater than the preset threshold $I_{OMAX}$, and an OR circuit 59 that sends a jump non-permission signal when the X-axis overcurrent signal or the Y-axis overcurrent signal is input to the address jump control section 55, but the other construction of this embodiment is similar to the fifth embodiment, and hence like parts are identified by like symbols while omitting a detailed explanation thereof.

In the above-mentioned fifth and sixth embodiments, the spiral phase is made variable at the start time point of a spiral period, i.e., when the amplitude of the exciting current is zero, but there is a possibility that the exciting current becomes large due to a malfunction, an error of the sine wave data, etc. Accordingly, in the command value transmission part 25G of the seventh embodiment, when the exciting current is larger than the predetermined threshold $I_{OMAX}$, the jump of the address carried out at the spiral period start time point is made non-permissive through the OR circuit 59.

In such a particle beam therapeutic apparatus according to the seventh embodiment, when a rapid change in an exciting current is caused due to a malfunction, erroneous data, etc., the address is incremented as it is without permitting a jump of the address, so it is possible to prevent breakage of the electromagnet power supplies hundred and.

Embodiment 8

Figure 18:
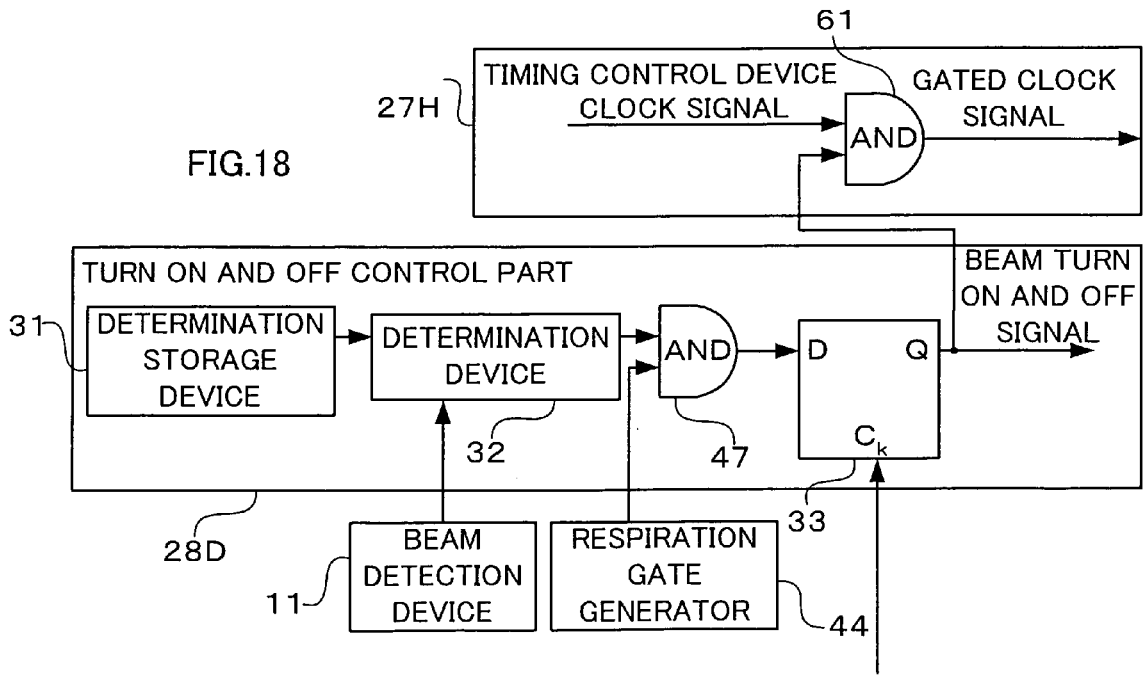
FIG. 18 is a block diagram of a timing control device and a turn on and off control part of a particle beam therapeutic apparatus according to an eighth embodiment of the present invention.

FIG. 18 is a block diagram of a timing control device and a turn on and off control part of a particle beam therapeutic apparatus according to an eighth embodiment of the present invention. The particle beam therapeutic apparatus according to the different eighth embodiment is different from the above-mentioned particle beam therapeutic apparatus 1D according to the fourth embodiment in a timing control device 27H, but the other construction of this embodiment is similar to the fourth embodiment, and hence like components or parts are identified by like symbols while omitting a detailed explanation thereof.

The timing control device 27H according to the eighth embodiment has an AND circuit 61 added to the timing control device 27 according to the fourth embodiment. A beam turn on and off signal from the register 33 of the turn on and off control part 28D and a clock signal of a preset clock period W are input to the AND circuit 61, and a gated clock signal is output from the AND circuit 61 to the data storage part 26. The address of the data storage part 26 is incremented by this gated clock signal.

In case where the respiration of a patient is not in a state in which the patient can be irradiated with a particle beam when the apparatus is operated in synchronization with the patient's respiration, the beam turn on and off signal becomes "LOW", whereby the gated clock signal input to the data storage part 26 is blocked, and the address thereof is not incremented. In this case, the exciting current is held as it is and hence irradiation is not carried out, but if a particle beam is supplied, the position of irradiation thereof does not move. Thus, when the patient's respiration is not stabilized, the supply of the particle beam is stopped and at the same time the state of excitation is maintained as it is. On the other hand, when the patient's respiration becomes stabilized, the beam gate signal changes into a "HIGH" level, and the gated clock signal is input to the data storage part 26, whereby scanning is resumed from the position at which the particle beam has been stopped.

In such a particle beam therapeutic apparatus as constructed above, even in cases where irradiation cannot be performed in a sufficiently large number of spiral periods such as when the irradiation time is short, when the dose rate is high, when the apparatus is in the respiration synchronized operation, or the like, the deflecting condition for the particle beam remains unchanged during the time when the particle beam is interrupted. As a result, there will be no tracks or loci along which irradiation is not carried out, thus making it possible to ensure the uniformity of dose distribution.

In addition, if the beam turning on and off control is carried out at the end time point of the spiral period, the amplitude of the exciting current becomes zero so the power consumption can be reduced.

Moreover, since the time occupied by acceleration and deceleration in the operation of the accelerator is longer than the beam turn-on time, a significant power saving effect can be obtained by adjusting the amplitude of the exciting current during acceleration and deceleration to zero.

Although in the eighth embodiment, the beam turn on and off signal is controlled in units of the spiral period, there will similarly be generated no track or locus containing a non-irradiated portion even if the particle beam is turned on and off and the gated clock signal is oscillated or stopped in immediate response to the patient's respiratory state based on the respiration gate signal during the spiral period.

Further, although in the eighth embodiment, the spiral phase is not made variable at the spiral period start time point, the clock signal can be controlled based on the respiration gate signal generated in accordance with the respiration synchronized operation while making variable the spiral phase at the spiral period start time point, as in the above-mentioned fifth and sixth embodiments.

Embodiment 9

Figure 19:
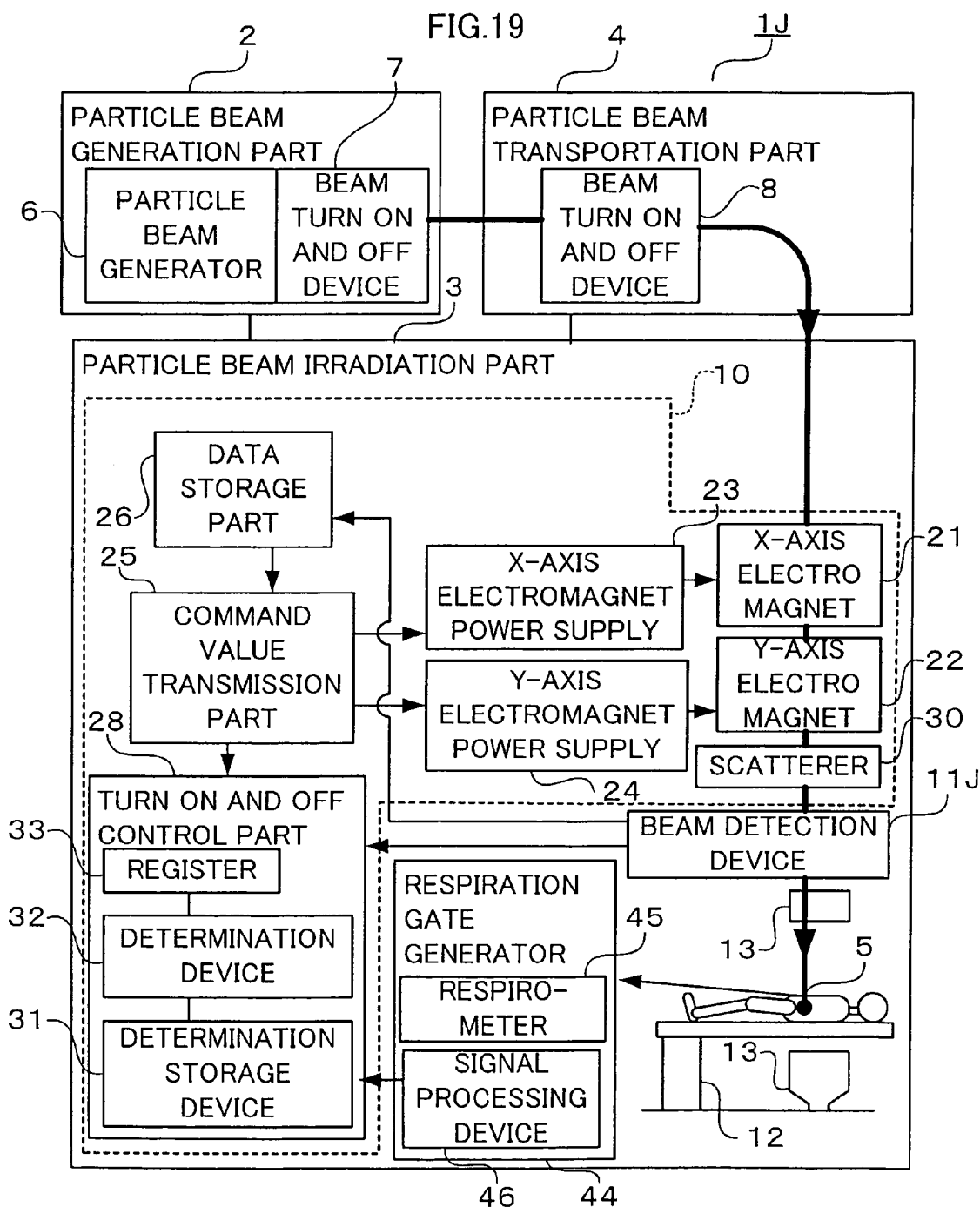
FIG. 19 is a block diagram showing a particle beam therapeutic apparatus according to a ninth embodiment of the present invention.
Figure 20:
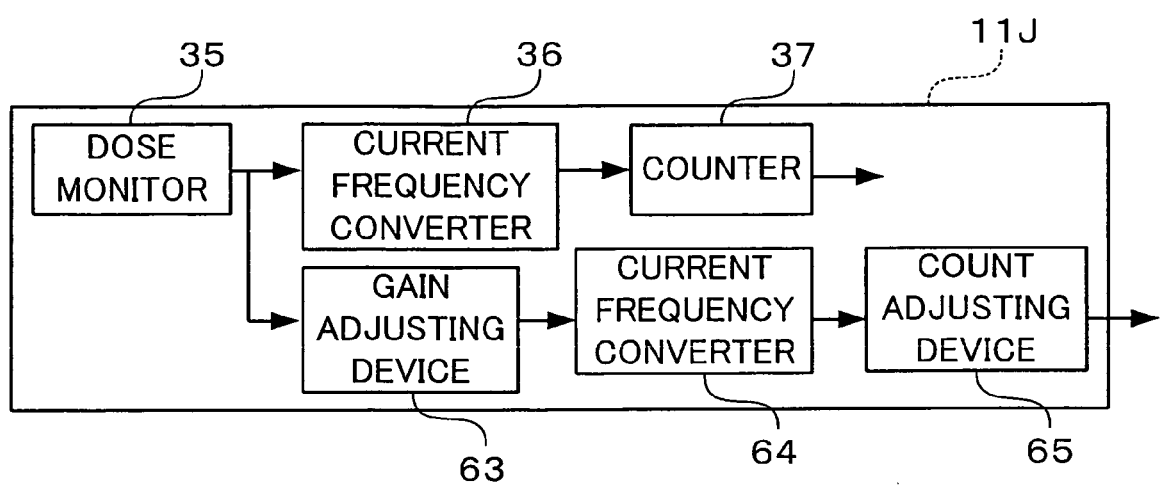
FIG. 20 is a block diagram of a beam detection device according to the ninth embodiment of the present invention.

FIG. 19 is a block diagram that shows a particle beam therapeutic apparatus according to a ninth embodiment of the present invention. FIG. 20 is a block diagram of a beam detection device according to the ninth embodiment of the present invention. As shown in FIG. 19, the particle beam therapeutic apparatus 1J according to the ninth embodiment is different from the above-mentioned particle beam therapeutic apparatus 1D according to the fourth embodiment in a beam detection device 11J and the omission of the timing control device 27, but the other construction of this ninth embodiment is similar to the fourth embodiment, and hence like components or parts are identified by like symbols while omitting a detailed explanation thereof. In the fourth embodiment, the address of the data table is incremented by a clock signal from the timing control device 27, but in the ninth embodiment, it is incremented by a clock signal proportional to an exposure or irradiation dose from the beam detection device 11J. The beam detection device 11J according to the ninth embodiment includes, as shown in FIG. 20, in addition to the dose monitor 35, the current frequency converter 36 and the counter 37 for obtaining the exposure dose, a gain adjusting device 63, a current frequency converter 64 and a count adjusting device 65 for creating a clock signal proportional to the exposure dose.

The gain adjusting device 63 is set in such a manner that the ratio of signal/noise is made to be the largest within an allowable range so as to increase the value of current input to the current frequency converter 64, thereby making it possible to create one pulse with the passage of the smallest possible electric charge.

The current frequency converter 64 serves to convert the current input thereto into a pulse train of a frequency proportional to the current value thus amplified. Here, note that since the current to be input to the current frequency converter 64 is amplified by the gain adjusting device 63, the frequency of the pulse train thus obtained becomes high.

The count adjusting device 65 serves to convert the pulse train into a frequency so as to create a pulse train corresponding to the number of divisions of a spiral period.

The beam detection device 11J has a function of creating a clock signal and a function of managing the total dose irradiated to a patient, and hence it is necessary to provide an appropriate safety measure to the beam detection device 11J.

For such a safety measure, it is proposed that systems for the respective functions are provided independently of each other, and each system for each function is multiplexed and has a function to mutually make a check between the systems.

In this particle beam therapeutic apparatus 1J, the address is not incremented until the dose irradiated to a certain irradiation position reaches an amount at which one clock signal is issued from the count adjusting device 65. Accordingly, the dose at each irradiation position is adjusted to meet a predetermined amount (i.e., the amount at which one clock signal is issued from the count adjusting device 65 ), so the exposure dose at each irradiation position is adjusted to accurately meet the predetermined amount over an entire target area.

In addition, even if the beam current supplied from the particle beam generation part 2 varies, the exposure dose is not influenced by the variation of the beam current since the irradiation position is moved not according to the time elapsed but when the exposure dose actually irradiated reaches an amount of dose corresponding to one clock signal.

Embodiment 10

Figure 21:
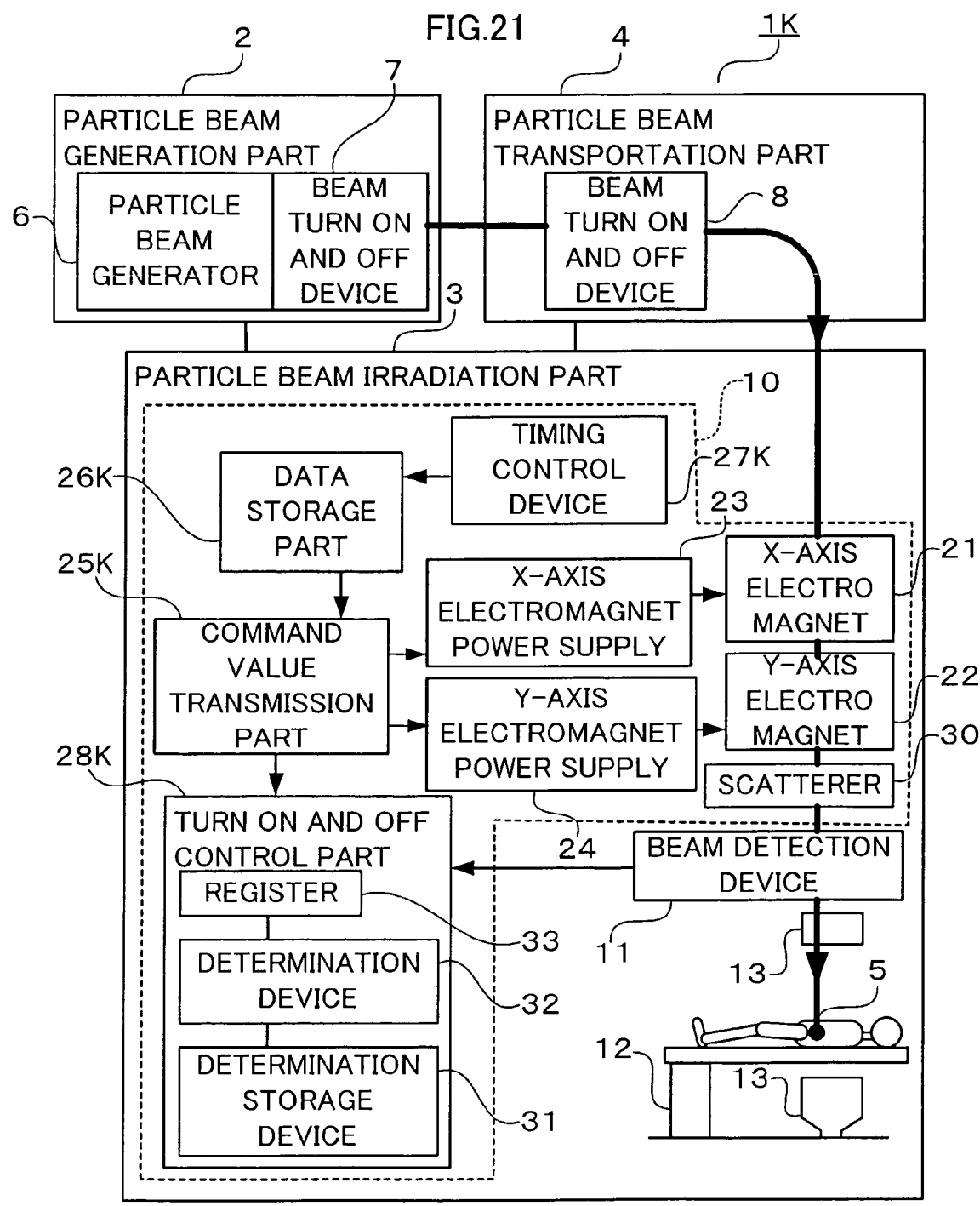
FIG. 21 is a block diagram showing a particle beam therapeutic apparatus according to a tenth embodiment of the present invention.
Figures 22, 23:
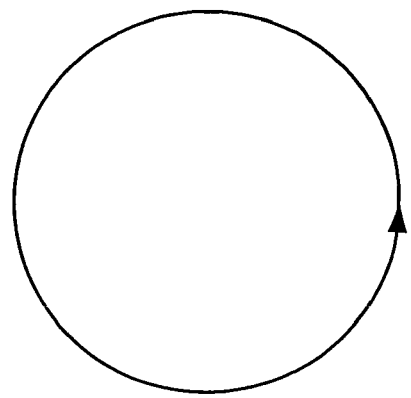
FIG. 22 is a view showing a circular locus.
FIG. 23 is a view showing the data structure of a data table stored in a data storage part according to the tenth embodiment of the present invention.

FIG. 21 is a block diagram that shows a particle beam therapeutic apparatus according to a tenth embodiment of the present invention. FIG. 22 is a view showing a circular track or locus. FIG. 23 is a view showing the data structure of a data table stored in a data storage part according to the tenth embodiment of the present invention. The particle beam therapeutic apparatus 1K according to the tenth embodiment is different from the above-mentioned particle beam therapeutic apparatus 1 according to the first embodiment in the track or locus of the irradiation of a particle beam, but the other construction of this tenth embodiment is similar to the first embodiment, and hence like components or parts are identified by like symbols while omitting a detailed explanation thereof. In relation to the particle beam locus difference, the particle beam therapeutic apparatus 1K according to the tenth embodiment is different from the particle beam therapeutic apparatus 1 according to the first embodiment in a data storage part 26K, a command value transmission part 25K, a timing control device 27K, and a turn on and off control part 28K, as shown in FIG. 21. In the first embodiment, the particle beam is scanned in a manner to draw a spiral locus, but in this tenth embodiment, the particle beam is scanned so as to draw a circular locus, as shown in FIG. 22. To this end, a data table in the data storage part 26K has three data areas and one pointer area that are set with respect to each of the addresses of sequential numbers, as shown in FIG. 23, and an X-axis exciting current designated value and a Y-axis exciting current designated value are stored in two data areas. Also, the remaining one data area is called a wobbler period end bit, in which data indicating the end or termination of a wobbler period is stored, and "1" is stored therein at the address of the end or termination of the wobbler period, whereas "0" is stored therein at other addresses.

In addition, "1" is stored in a pointer area corresponding to an address that is incremented based on a clock signal, whereas "0" is stored in pointer areas corresponding to the other addresses. The data in a data area at an address whose pointer area has "1" stored therein is sent to the command value transmission part 25K.

The X-axis exciting current designated value and the Y-axis exciting current designated value are calculated based on the following expressions (14) and (15) at each predetermined clock period W that equally divides the wobbler period $T_W$ into p parts, and stored in the data storage part 26K. For example, assuming that the wobbler period $T_W$ is 18 milliseconds and is equally divided into 36 parts, the clock period W is 0.5 milliseconds, and 36 addresses are occupied by one wobbler period $T_W$. Assuming that the addresses are from 0 to 35, "1" is stored in the wobbler period end bit at an address of 35.

$$I_X = \sin(\omega t + \phi_0) \quad (14)$$

$$I_Y = \cos(\omega t + \phi_0) \quad (15)$$

In the data storage part 26K, the address is incremented each time a clock signal is input thereto, and the data of an X-axis exciting current designated value, a Y-axis exciting current designated value and a wobbler period end bit stored at that address are read and sent to the command value transmission part 25K.

The command value transmission part 25K sends an X-axis exciting current command value to the X-axis electromagnet power supply 23, and a Y-axis exciting current command value to the Y-axis electromagnet power supply 24 based on the X-axis exciting current designated value and the Y-axis exciting current designated value, respectively, sent from the data storage part 26K. Further, when the data of the wobbler period end bit is determined as "1" based on the data of the wobbler period end bit sent from the data storage part 26K, the command value transmission part 25K sends a pulse, which sequentially changes into a "LOW", a "HIGH" and a "LOW" level, to the turn on and off control part 28K as a wobbler period end signal.

The timing control device 27K inputs a clock signal of a clock period W obtained from the wobbler period $T_W$ and the p equally divided parts thereof, and a reset signal to restore the address of the data storage part 26K to the first address to the data storage part 26K.

The turn on and off control part 28K includes a determination storage device 31 in which a planned dose set prior to a treatment by particle beam irradiation is stored, a determination device 32 that compares the exposure dose from the beam detection device 11 and the planned dose, determines the presence or absence of a beam request, and changes the level of a beam request signal, and a register 33 that sends the level of the beam request signal to the beam turn on and off devices 7, 8 at each breakpoint or end of the wobbler period as a beam turn on and off signal. The beam request signal is at a "HIGH" level in the presence of a beam request, and at a "LOW" level in the absence of a beam request.

In the register 33, when a pulse in the form of a wobbler period end signal is input to a CLOCK terminal thereof, the level of the beam request signal input to a D input terminal thereof is output from a Q output terminal thereof as a beam turn on and off signal.

Even if the exposure dose exceeds the planned dose during a certain wobbler period thereby to change the level of the beam request signal into a "LOW" level, the level of the beam turn on and off signal remains "HIGH" as long as a pulse in the form of a spiral period end signal is not input to the register 33. When a pulse in the form of a wobbler period end signal is sent from the command value transmission part 25K, the level of the beam turn on and off signal first changes into a "LOW" level, whereby the particle beam is interrupted.

In this particle beam therapeutic apparatus, the irradiation of the particle beam is not interrupted during the wobbler period, so it is possible to ensure the uniformity of dose distribution.

Figure 24:
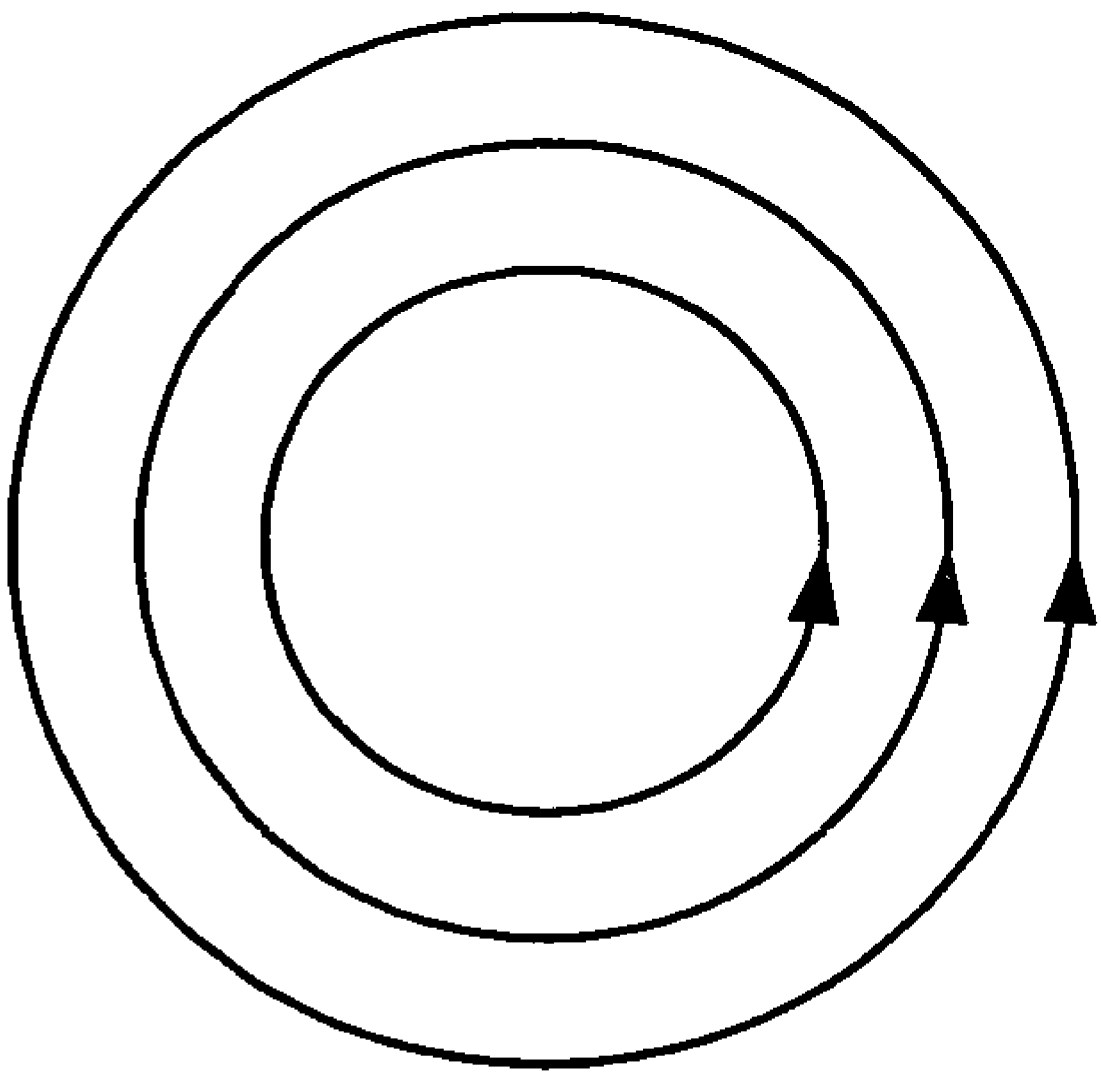
FIG. 24 is a view showing a plurality of circular loci of concentric circles.

In addition, in the case of a wobbler irradiation method using a plurality of circles as shown in FIG. 24 or when the exposure rate is made large, the uniformity of dose distribution can be easily ensured even with irradiation for a short time by carrying out the irradiation in units of the wobbler period.

Moreover, although a method of performing scanning in a continuous manner while continuing irradiation, a method of starting irradiation of a beam after the beam has been moved with the irradiation of the beam being once stopped temporarily, a method of repeating the movement and stoppage of a beam while continuing irradiation, etc., are known as beam irradiation according to a wobbler method, either of these methods can be applied to the particle beam therapeutic apparatus 1K of the present invention.

Embodiment 11

Figure 25:
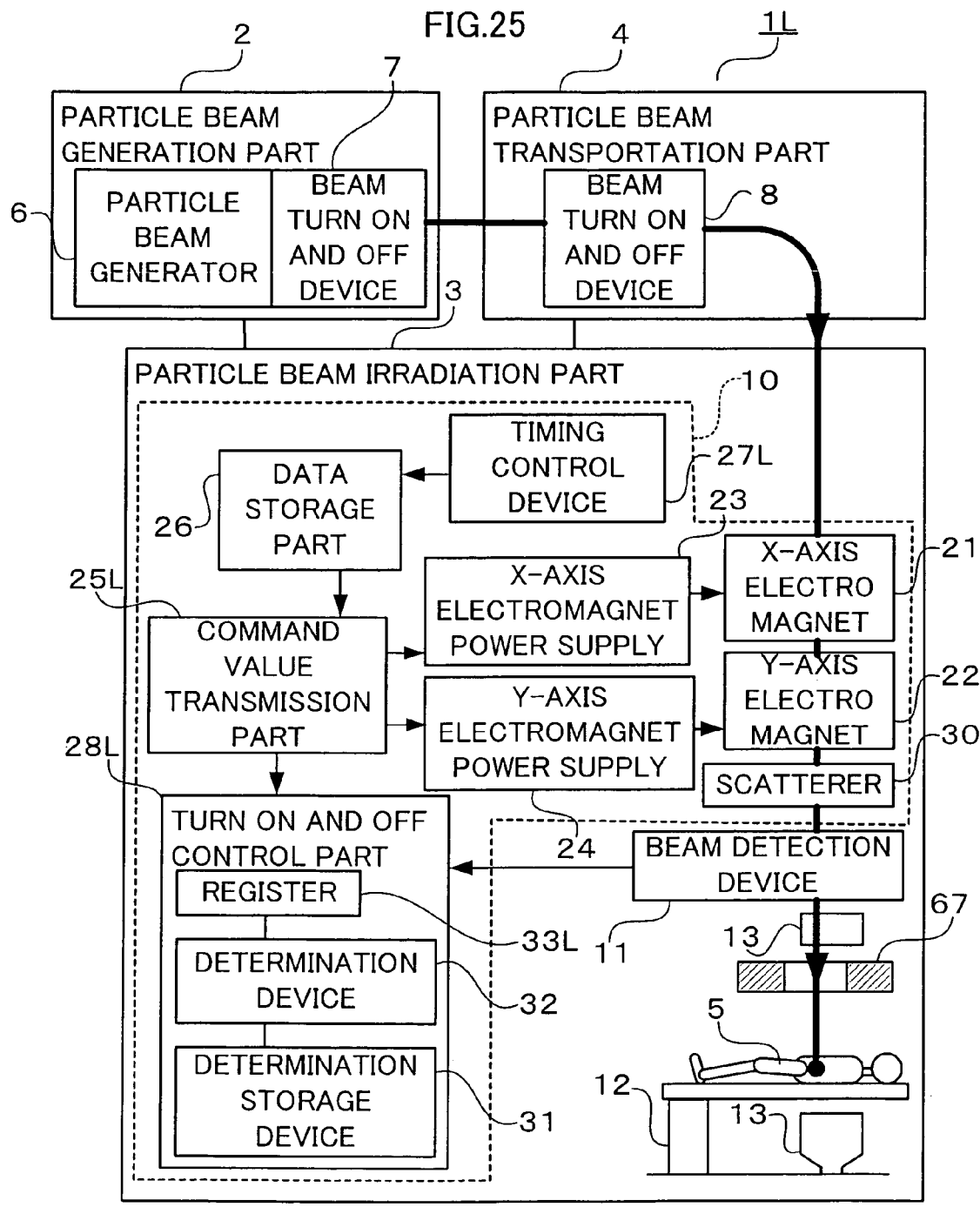
FIG. 25 is a block diagram showing a particle beam therapeutic apparatus according to an eleventh embodiment of the present invention.
Figure 26:
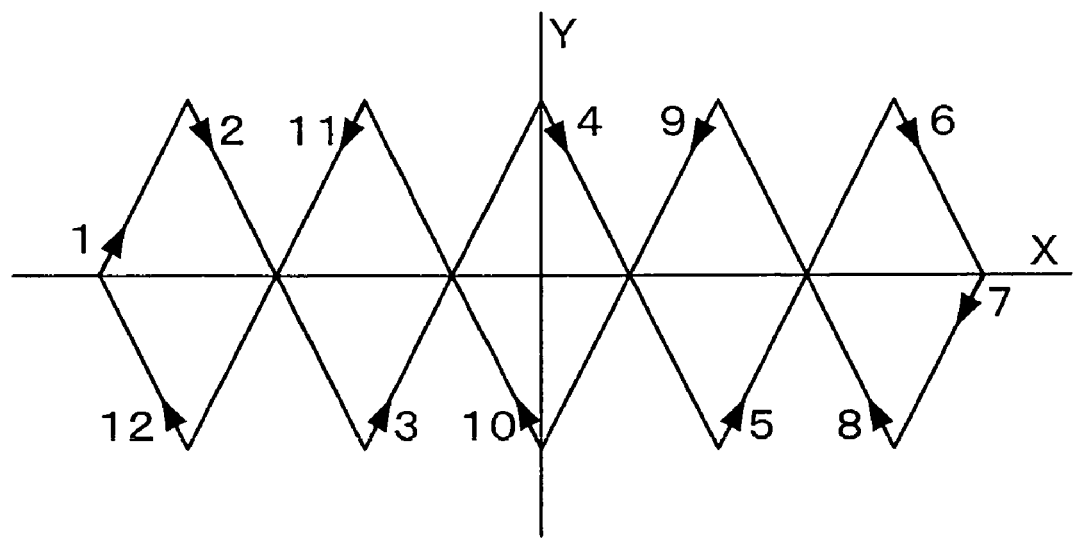
FIG. 26 is a view showing an example of a zigzag locus.
Figure 27:
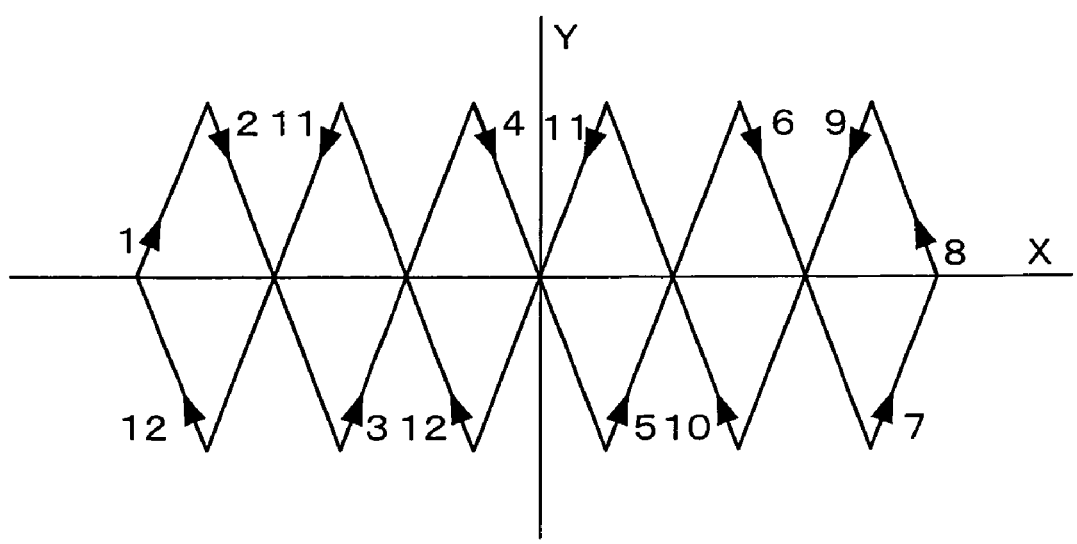
FIG. 27 is a view showing an example of another zigzag locus.

FIG. 25 is a block diagram that shows a particle beam therapeutic apparatus according to an eleventh embodiment of the present invention. FIG. 26 is a view showing an example of a zigzag locus. FIG. 27 is a view showing an example of another zigzag locus. The particle beam therapeutic apparatus 1L according to the eleventh embodiment is different from the above-mentioned particle beam therapeutic apparatus 1 according to the first embodiment in the track or locus of the irradiation of a particle beam, as shown in FIG. 25, but the other construction of this eleventh embodiment is similar to the first embodiment, and hence like components or parts are identified by like symbols while omitting a detailed explanation thereof. In relation to the particle beam locus difference, the particle beam therapeutic apparatus 1L according to the eleventh embodiment is different from the particle beam therapeutic apparatus 1 according to the first embodiment in a data storage part 26L, a command value transmission part 25L, a timing control device 27L, and a turn on and off control part 28L.

Also, a beam interruption device in the form of a multileaf collimator device 67 is added which serves to interrupt a particle beam scanned around the field of irradiation. A four-leaf collimator device, a block collimeter device, etc., can be used as such a beam interruption device, other than the multileaf collimator device 67. The beam interruption device serves to shield the particle beam when the scanning of the beam is turned back around the irradiation field. In the first embodiment, the particle beam is scanned so as to draw a spiral locus, but in the eleventh embodiment, the particle beam is scanned in such a manner that it draws a zigzag locus in which five round trips are made in the Y-axis direction during one round trip in the X-axis direction, as shown in FIG. 26. To this end, a data table in the data storage part 26L has three data areas and one pointer area that are set with respect to each of the addresses of sequential numbers, and an X-axis exciting current designated value and a Y-axis exciting current designated value are stored in two data areas. Also, the remaining one data area is called an X-axis direction period end bit, in which is stored data indicating the termination or end of the X-axis direction period in which one round trip in the X-axis direction is made. "1" is stored at an address of the termination or end of the X-axis direction period, whereas "0" is stored at other addresses.

In addition, "1" is stored in a pointer area corresponding to an address that is incremented based on a clock signal, whereas "0" is stored in pointer areas corresponding to the other addresses. The data in a data area at an address whose pointer area has "1" stored therein is sent to the command value transmission part 25L.

The X-axis exciting current designated value and the Y-axis exciting current designated value are calculated at each predetermined clock period W that equally divides the X-axis direction period $T_X$ into q parts, and stored in the data storage part 26L.

In the data storage part 26L, the address is incremented each time a clock signal is input thereto, and the data of an X-axis exciting current designated value, a Y-axis exciting current designated value and an X-axis direction period end bit stored at that address are read and sent to the command value transmission part 25L.

The command value transmission part 25L sends an X-axis exciting current command value to the X-axis electromagnet power supply 23 and a Y-axis exciting current command value to the Y-axis electromagnet power supply 24 based on the X-axis exciting current designated value and the Y-axis exciting current designated value, respectively, sent from the data storage part 26L. Further, when the data of the X-axis direction period end bit is determined as "1" based on the data of the X-axis direction period end bit sent from the data storage part 26L, the command value transmission part 25L sends a pulse, which sequentially changes into a "LOW", a "HIGH" and a "LOW" level, to the turn on and off control part 28L as an X-axis direction period end signal.

The timing control device 27L inputs a clock signal of a clock period W obtained from the wobbler period $T_W$ and the q equally divided parts thereof, and a reset signal to restore the address of the data storage part 26L to the first address to the data storage part 26L.

The turn on and off control part 28L includes a determination storage device 31 in which a planned dose set prior to a treatment by particle beam irradiation is stored, a determination device 32 that compares the exposure dose from the beam detection device 11 and the planned dose, determines the presence or absence of a beam request, and changes the level of a beam request signal, and a register 33L that sends the level of the beam request signal to the beam turn on and off devices 7, 8 at each breakpoint or end of the X-axis direction period as a beam turn on and off signal. The beam request signal is at a "HIGH" level in the presence of a beam request, and at a "LOW" level in the absence of a beam request.

In the register 33L, when a pulse in the form of an X-axis direction period end signal is input to a CLOCK terminal thereof, the level of the beam request signal input to a D input terminal thereof is output from a Q output terminal thereof as a beam turn on and off signal.

Even if the exposure dose exceeds the planned dose during a certain X-axis direction period thereby to change the level of the beam request signal into a "LOW" level, the level of the beam turn on and off signal remains "HIGH" as long as a pulse in the form of an X-axis direction period end signal is not input to the register 33L. When a pulse in the form of an X-axis direction period end signal is sent from the command value transmission part 25L, the level of the beam turn on and off signal first changes into a "LOW" level, whereby the particle beam is interrupted.

In this particle beam therapeutic apparatus 1L, the irradiation of the particle beam is not interrupted during the X-axis direction period, so it is possible to ensure the uniformity of dose distribution.

In addition, in the case of an irradiation method using an increased number of zigzags as shown in FIG. 27 or when the exposure rate is made large, the uniformity of dose distribution can be easily ensured even with irradiation for a short time by carrying out the irradiation in units of the X-axis direction.

Moreover, although a method of performing scanning in a continuous manner while continuing irradiation, a method of starting irradiation of a beam after the beam has been moved with the irradiation of the beam being once stopped temporarily, a method of repeating the movement and stoppage of a beam while continuing irradiation, etc., are known as beam irradiation according to a zigzag irradiation method, either of these methods can be applied to the particle beam therapeutic apparatus 1L of the present invention.

Further, although in the eleventh embodiment, the address of the data storage part 26L is incremented by a clock signal from the timing control device 27L, there can be added a function of interrupting the increment of the address when the level of the beam turn on and off signal becomes "LOW" and the supply of the particle beam is interrupted, as described in the above-mentioned eighth embodiment.

Furthermore, the increment of the address can be controlled by using a clock signal created based on a beam current value of a dose monitor, as described in the above-mentioned ninth embodiment.

Embodiment 12

Figure 28:
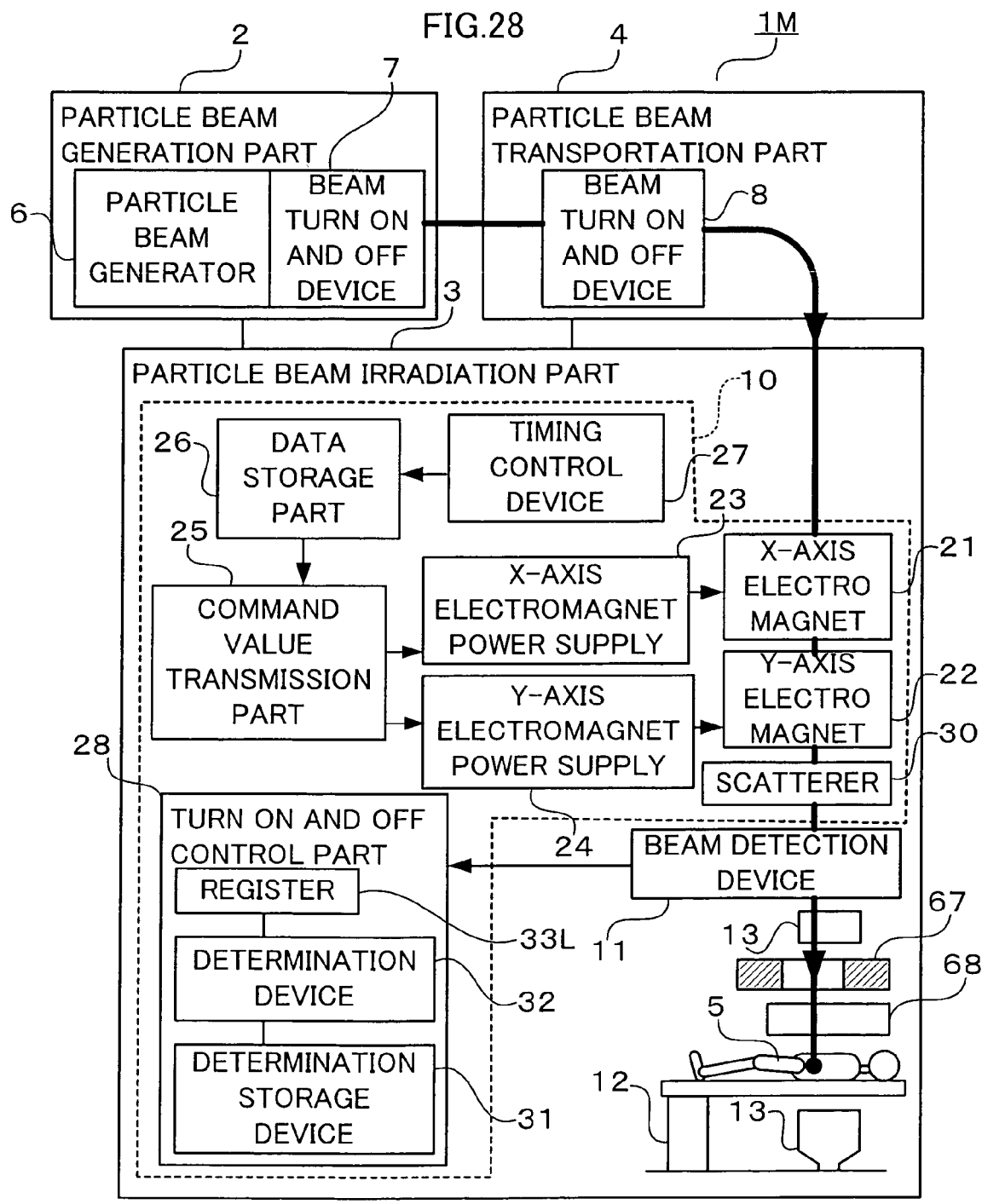
FIG. 28 is a block diagram showing a particle beam therapeutic apparatus according to a twelfth embodiment of the present invention.

FIG. 28 is a block diagram that shows a particle beam therapeutic apparatus according to a twelfth embodiment of the present invention. The particle beam therapeutic apparatus 1M according to the twelfth embodiment includes, as shown in FIG. 28, a beam interruption device in the form of a multileaf collimator device 67 and a particle beam energy changing device in the form of a range shifter device 68, which are added to the above-mentioned particle beam therapeutic apparatus 1 according to the first embodiment, but the other construction of this twelfth embodiment is similar to the first embodiment, and hence like components or parts are identified by like symbols while omitting a detailed explanation thereof.

Here, note that the energy of a particle beam can be changed by changing the set value of the energy of a synchrotron type accelerator in the particle beam generation part 2, other than by using the range shifter device 68 as a particle beam energy changing device. In addition, the energy of a particle beam can also be changed by changing an exciting current for a coil of an unillustrated electromagnet in the particle beam transportation part 4. Thus, the present invention is not limited to the use of the range shifter device 68.

The range shifter device 68 is composed of polyethylene, and serves to decrease the energy of a particle beam up to a desired value by passing part of the particle beam through the range shifter device 68. Thus, by variably changing the energy of the particle beam, it is possible to adjust the depth that the particle beam can reach, so that a desired planned dose is irradiated to each of target layers stratified in the direction of depth so as to provide a desired dose distribution in a three-dimensional manner. This is called a layer-stacking conformal irradiation method.

Since a three-dimensional target region has a plurality of planar target areas of varying shapes which are layered or stratified in the direction of depth and which are cross-sectioned in a direction perpendicular to the direction of depth, the multileaf collimator device 67, acting as a beam interruption device, is provided for the purpose of irradiating a particle beam to each planar target area of a specific shape alone. Here, note that as such a beam interruption device, there are a four-leaf collimator device, a block collimeter device, etc., any of which can also be applied or used for the purpose of the present invention, other than the multileaf collimator device 67.

The multileaf collimator device 67 has its opening set to an optimal configuration or shape of a target layer to be irradiated which is determined beforehand.

Next, reference will be made to the irradiation of a particle beam carried out in units of a spiral period according to the layer-stacking conformal irradiation method.

First, prior to a treatment by using a particle beam, a three-dimensional target region is layered or stratified into a plurality of layers each having a thickness of about 5 mm-10 mm by means of parallel planes perpendicular to the direction of irradiation of the particle beam, and a planned dose is set for each of the layers and stored in the determination storage device 31. In addition, the outer shape of the target region in each layer is measured, and appropriate set values or parameters are determined beforehand so as to form the opening of the multileaf collimator device 67 into an optimum shape or configuration for the outer shape of the target region in each layer. Also, a plurality of range shifter devices 68 suitable for irradiation on the respective layers are prepared prior to the treatment.

An appropriate range shifter device 68 is set or installed so as to irradiate one layer, and the multileaf collimator device 67 is adjusted to properly define the shape of its opening, whereby a particle beam is irradiated to the one layer by overlapping or superposing the spiral loci up to a planned dose for that layer, as previously explained in the first embodiment. At this time, the turning on and off of the particle beam is carried out in units of the spiral period, and the particle beam should never be turned off during each spiral period.

Then, in order to irradiate the following layer, another appropriate range shifter device 68 is installed, and the multileaf collimator device 67 is adjusted again to properly define the shape of its opening, after which the following irradiation is carried out. By repeating this procedure, a three-dimensional diseased part can be irradiated in a layered or stratified fashion by using the layer-stacking conformal irradiation method.

In this particle beam therapeutic apparatus 1M, the layer-stacking conformal irradiation method is used to control the irradiation of the particle beam in the direction of depth of the diseased part, whereby an advantageous effect is provided in which a three-dimensional dose distribution can be obtained. Also, in terms of the dose, by dividing the diseased part into the plurality of layers in the direction of depth thereof, the amount of dose irradiated to each layer can be decreased to a substantial extent. For example, in case where a diseased part of a thickness of 10 cm in the direction of depth thereof is divided into 20 layers, it is known that if a dose in units of 100 is irradiated to the deepest layer, a layer that is shallower than the deepest one typically requires only an amount of dose equal to 10 units or less, i.e., one digit smaller than that for the deepest layer. In general, with respect to layers on a shallow side other than the deepest layer, the amount of dose required to be irradiated can be considerably small resulting from the physical property of the particle beam. Consequently, the irradiation time for these shallow layers becomes considerably short, and hence according to conventional methods, it is difficult to guarantee the horizontal uniformity (i.e., uniformity in a direction perpendicular to the direction of irradiation) of dose distribution.

In case where the layer-stacking conformal irradiation method is combined with respiration synchronized operation, it becomes further difficult to obtain the uniformity of dose distribution.

In contrast to this, by applying each of the constructions of the above-mentioned first through eleventh embodiments to the layer-stacking conformal irradiation method, it is possible to satisfy the more severe conditions of the layer-stacking conformal irradiation method and to ensure the uniformity of dose distribution.

Although in the twelfth embodiment a particle beam is scanned so as to draw spiral loci, the irradiation of a particle beam to each layer in the layer-stacking conformal irradiation method may also be carried out in such a manner that the particle beam can be scanned so as to draw circular loci or zigzag loci.

Embodiment 13

Figure 29:
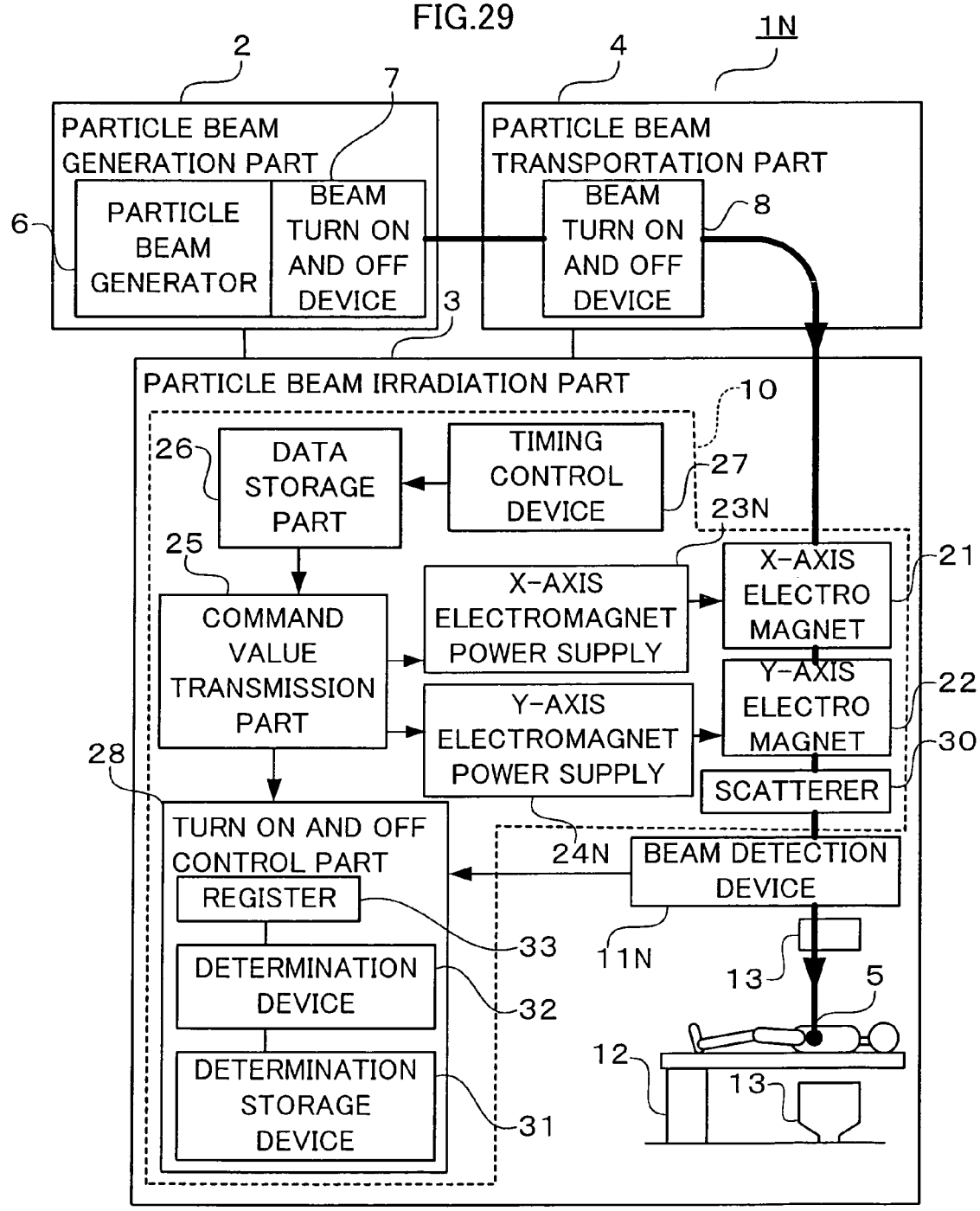
FIG. 29 is a block diagram showing a particle beam therapeutic apparatus according to a thirteenth embodiment of the present invention.
Figure 30:
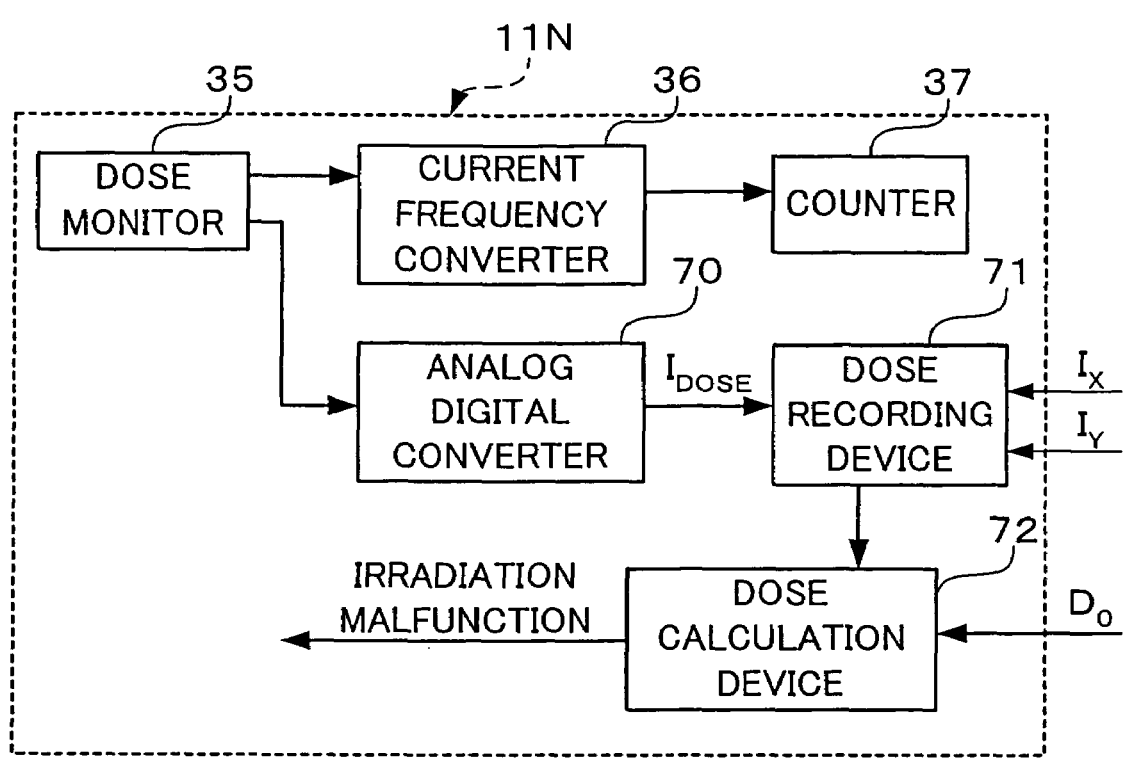
FIG. 30 is a block diagram of a beam detection device according to the thirteenth embodiment of the present invention.
Figure 31:
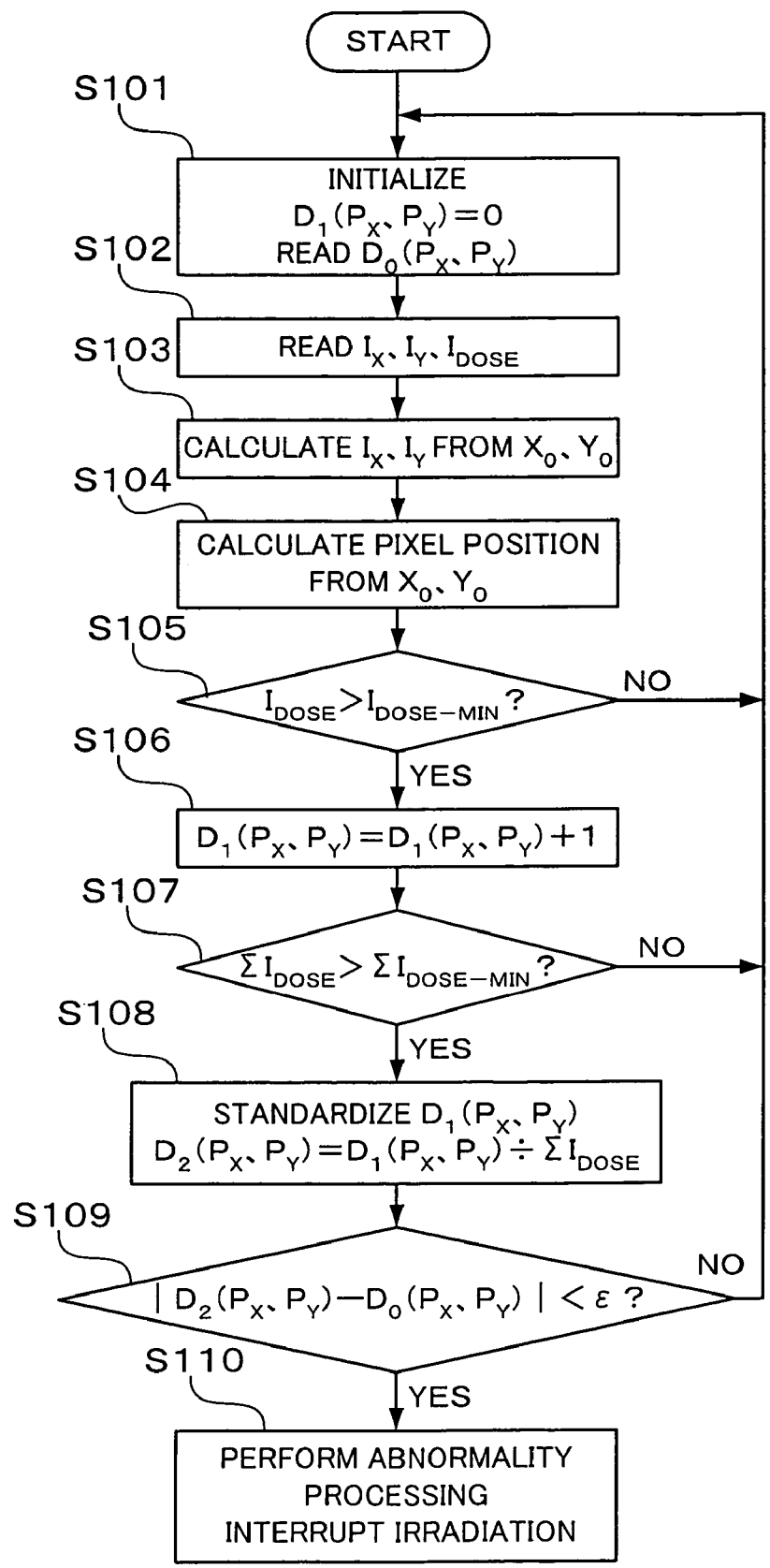
FIG. 31 is a flow chart showing a procedure for monitoring an exposure or irradiation dose in the particle beam therapeutic apparatus according to the thirteenth embodiment of the present invention.

FIG. 29 is a block diagram that shows a particle beam therapeutic apparatus according to a thirteenth embodiment of the present invention. FIG. 30 is a block diagram of a beam detection device according to the thirteenth embodiment of the present invention. FIG. 31 is a flow chart that shows a procedure for monitoring an exposure or irradiation dose in the particle beam therapeutic apparatus according to the thirteenth embodiment of the present invention. The particle beam therapeutic apparatus 1N according to the thirteenth embodiment is different from the above-mentioned particle beam therapeutic apparatus 1 according to the first embodiment in the addition thereto of a function to obtain the coordinates information of an irradiation position and a function to determine whether the exposure dose of the irradiation position is appropriate, as shown in FIG. 29, but the other construction of this embodiment is similar to the first embodiment, and hence like components or parts are identified by like symbols while omitting a detailed explanation thereof.

An X-axis electromagnet power supply 23N and a Y-axis electromagnet power supply 24N according to the thirteenth embodiment are each provided at their output with an unillustrated ammeter for measuring an excitation current value. An X-axis exciting current $I_X$ and a Y-axis exciting current $I_Y$ are output from these ammeters.

In addition, the beam detection device 11N according to the thirteenth embodiment has the following components added to the beam detection device 11 according to the first embodiment, as shown in FIG. 30. That is, the beam detection device 11N includes an analog digital converter 70 for converting a beam current of the dose monitor 35 into a digitalized dose monitor output $I_{DOSE}$, a dose recording device 71 that records the X-axis exciting current $I_X$, the Y-axis exciting current $I_Y$ and the dose monitor output $I_{DOSE}$ in time series, and a dose calculation device 72 that determines whether an exposure dose coincides with a prescribed planned dose, and warns an abnormality or malfunction to the outside in case of non-coincidence therebetween.

Next, reference will be made to the procedure for monitoring the exposure dose in the particle beam therapeutic apparatus according to the thirteenth embodiment while referring to FIG. 31.

A two-dimensional exposure or irradiation area at each irradiation depth is divided or partitioned into squares of pixels of 5 mm×5 mm in a matrix fashion for example, and the management of irradiation is performed in units of a pixel.

In step S101, the count values $D_1$ ($P_X$, $P_Y$) of each pixel ($P_X$, $P_Y$) is cleared to zero, and prescribed pixel set values $D_0$ ($P_X$, $P_Y$) are read from the outside.

In step S102, an X-axis exciting current $I_X$, a Y-axis exciting current $I_Y$ and an output $I_{DOSE}$ of the dose monitor 35 are recorded in time series into the dose recording device 71 during irradiation. For example, a recording time interval is set to be sufficiently short, e.g., 0.1 milliseconds, with respect to the movement of an electromagnet.

In step S103, the values of $I_X$, $I_Y$ at the time interval are read, and an X coordinate $X_0$ and a Y coordinate $Y_0$ in the center of a beam at an irradiation depth are calculated from these values.

In step S104, the coordinates $P_X$, $P_Y$ of a pixel corresponding to the X coordinate $X_0$ and the Y coordinate $Y_0$ are obtained.

In step S105, when the value of $I_{DOSE}$ is equal to or larger than a prescribed threshold $I_{DOSE-MIN}$, the control flow advances to S106 whereas when the value of $I_{DOSE}$ is less than the prescribed threshold $I_{DOSE-MIN}$, a return to step S102 is carried out.

In step S106, the count values $D_1$ ($P_X$, $P_Y$) of $P_X$, $P_Y$ are incremented by 1, respectively, according to the following expression (16).

$$D_1(P_X, P_Y) = D_1(P_X, P_Y) + 1 \tag{16}$$

In step S107, it is determined whether a certain amount of distributions has been recorded. That is, it is determined whether the time integrated value of the dose monitor $\Sigma I_{DOSE}$ has exceeded a prescribed integrated value threshold $\Sigma I_{DOSE-MIN}$, and when exceeded, the control flow advances to step S108, whereas when otherwise, a return to step S102 is carried out.

In step S108, the count values $D_1$ ($P_X$, $P_Y$) are standardized or normalized to provide standardized count values $D_2$ ($P_X$, $P_Y$). When a comparison is made between a measured distribution and a desired distribution, the count value accumulated in a matrix is standardized or normalized by a count value in the total area.

In step S109, the standardized count values $D_2$ ($P_X$, $P_Y$) are compared with the prescribed pixel set values $D_0$ ($P_X$, $P_Y$), respectively, that have been read from the outside. When a difference between the data of the pixels exceeds a preset range as a result of a pixel to pixel comparison, it is determined that the pixels thus compared are non-coincident with each other. When the number of non-coincident pixels exceeds a predetermined value, an abnormality flag is set up and the control flow advances to step S110, whereas when the number of non-coincident pixels is equal to or less than the predetermined value, a return to step S102 is carried out.

In step S110, the result thus obtained is notified to an operator.

Here, note that when the number of non-coincident pixels exceeds the predetermined value, the beam may be stopped temporarily at the same time.

In addition, the criterion to determine an abnormality or malfunction may be that the number of non-coincidences for one pixel exceeds a predetermined value. Also, the absolute value of a difference between data for each pixel is accumulated or integrated, and such a criterion may be that a total sum thereof is equal to or more than a threshold. Further, a combination of these conditions may be used.

Moreover, when the count value of the pixel is incremented, it may be incremented not by 1 count but instead by a count $kI_{DOSE}$ proportional to the current value of the dose monitor according to the following expression (17).

$$D_1(P_X, P_Y) = D_1(P_X, P_Y) + kI_{DOSE} \tag{17}$$

By incrementing the count value by a value which is proportional to the current value of the dose monitor in this manner, the value of the matrix will exhibit a distribution near an actual dose distribution, so a determination can be made based on more accurate information.

In this particle beam therapeutic apparatus 1N, safety can be verified based on the records of the apparatus during the actual irradiation, so even if irradiation control with the above-mentioned optional functions of the first through thirteenth embodiments is performed, safety will not be impaired.

While the invention has been described in terms of preferred embodiments, those skilled in the art will recognize that the invention can be practiced with modifications within the spirit and scope of the appended claims.

What is claimed is:

1. A particle beam therapeutic apparatus in which a flow of a particle beam transported so as to be irradiated to a diseased part is caused to deflect in two mutually orthogonal directions perpendicular to the direction of travel of said particle beam, and the irradiation position of said particle beam is scanned, upon each period, in a manner to return to a position of irradiation located at the start of said period, whereby a plurality of loci drawn within one period are overlapped with one another thereby to irradiate a desired planned dose to said diseased part, wherein said particle beam can be interrupted only at the end of said period.

2. The particle beam therapeutic apparatus as set forth in claim 1, wherein when the irradiation position of said particle beam is scanned in such a manner that said transported particle beam rotates at a predetermined angular velocity about a center at which said particle beam passes through a plane perpendicular to the direction of travel of said particle beam with a distance to said particle beam from said center being increased and decreased, the initial phase of the rotation of said particle beam at the start time point of said period can be made variable.

3. The particle beam therapeutic apparatus as set forth in claim 2, further comprising;

a storage section having a plurality of areas to which addresses are assigned, and in which amplitude data which is increased and decreased in said period when read out from said areas while said address is forwarded and designated progressively, and sine wave function data which oscillates at the said angular velocity in a sinusoidal manner when read out from said areas are stored in said plurality of areas;

a command value transmission part that sends a command in the form of the product of said amplitude data and said sine wave function data, which are read out from said areas at an address designated progressively each time a clock signal is input, to an X-axis electromagnet power supply as an X-axis exciting current command value, and also sends a command in the form of the product of said amplitude data and sine wave function data, which advances 90 degrees in phase from said sine wave function data, to a Y-axis electromagnet power supply as a Y-axis exciting current command value;

said X-axis electromagnet power supply that controls an X-axis exciting current supplied to an X-axis electromagnet based on said X-axis exciting current command value;

said Y-axis electromagnet power supply that controls a Y-axis exciting current supplied to a Y-axis electromagnet based on said Y-axis exciting current command value;

said X-axis electromagnet that deflects the flow of said transported particle beam toward an X-axis direction perpendicular to the direction of travel of said particle beam by said X-axis exciting current being supplied thereto; and said Y-axis electromagnet that deflects the flow of said transported particle beam toward a Y-axis direction perpendicular to the direction of travel of said particle beam by said Y-axis exciting current being supplied thereto.

4. The particle beam therapeutic apparatus as set forth in claim 2, wherein a storage section having a plurality of areas to which addresses are assigned, and in which sine wave function data from whose amplitude is repeatedly increased and decreased in said period and oscillates at said angular velocity when read out from said areas while said address is designated progressively, and cosine wave function data whose amplitude is repeatedly increased and decreased in said period with its phase advancing 90 degrees from said sine wave function data when read out from said areas are stored;

a command value transmission part that sends a command in the form of said sine wave function data, which are read out from said areas at an address designated progressively each time a clock signal is input, to an X-axis electromagnet power supply as an X-axis exciting current command value, and also sends a command in the form of said cosine wave function data to a Y-axis electromagnet power supply as a Y-axis exciting current command value;

said X-axis electromagnet power supply that controls an X-axis exciting current supplied to an X-axis electromagnet based on said X-axis exciting current command value;

said Y-axis electromagnet power supply that controls a Y-axis exciting current supplied to a Y-axis electromagnet based on said Y-axis exciting current command value;

said X-axis electromagnet that deflects the flow of said transported particle beam toward an X-axis direction perpendicular to the direction of travel of said particle beam by said X-axis exciting current being supplied thereto; and said Y-axis electromagnet that deflects the flow of said transported particle beam toward a Y-axis direction perpendicular to the direction of travel of said particle beam by said Y-axis exciting current being supplied thereto.

5. The particle beam therapeutic apparatus as set forth in claim 2, further comprising:

a storage section having a plurality of areas to which addresses are assigned, and in which amplitude data which is increased and decreased in said period when read out from said areas while said address is designated progressively, and periodical function data are stored in said plurality of areas;

a command value transmission part that sends a command in the form of the product of said amplitude data and said function data, which are read out from said areas at an address designated progressively each time a clock signal is input, to an X-axis electromagnet power supply as an X-axis exciting current command value, and also sends a command in the form of the product of said amplitude data and function data, which advances a predetermined phase from said function data, to a Y-axis electromagnet power supply as a Y-axis exciting current command value;

said X-axis electromagnet power supply that controls an X-axis exciting current supplied to an X-axis electromagnet based on said X-axis exciting current command value;

said Y-axis electromagnet power supply that controls a Y-axis exciting current supplied to a Y-axis electromagnet based on said Y-axis exciting current command value;

said X-axis electromagnet that deflects the flow of said transported particle beam toward an X-axis direction perpendicular to the direction of travel of said particle beam by said X-axis exciting current being supplied thereto; and said Y-axis electromagnet that deflects the flow of said transported particle beam toward a Y-axis direction perpendicular to the direction of travel of said particle beam by said Y-axis exciting current being supplied thereto.

6. The particle beam therapeutic apparatus as set forth in claim 1, further comprising:

a patient monitor device that monitors the state of a patient; and a beam turn on and off device that turns on and off said particle beam based on the state of said patient;

wherein by maintaining, upon turning off of said particle beam, an X-axis exciting current and a Y-axis exciting current flowing through said X-axis electromagnet and said Y-axis electromagnet at constant values, respectively, the scanning of said particle beam is resumed, upon turning on of said particle beam, from that position of said diseased part which was irradiated by said particle beam when said particle beam was turned off.

7. The particle beam therapeutic apparatus as set forth in claim 3, further comprising:

a dose monitor that measures a dose irradiated to said diseased part;

a beam detection device that sends a clock signal each time a predetermined dose has been irradiated; and a storage device whose address is advanced progressively by said clock.

8. The particle beam therapeutic apparatus as set forth in claim 3, further comprising:

a dose recording device that records an X-axis excitation current value, a Y-axis excitation current value, and a dose in a time series manner when said particle beam is turned on; and a dose calculation device that calculates an irradiation position from said X-axis excitation current value and said Y-axis excitation current value, and compares a dose at said irradiation position with a prescribed value.

9. The particle beam therapeutic apparatus as set forth in claim 8, wherein said dose calculation device compares a dose at each irradiation position with a described value, and warns an abnormal state when it makes a determination of abnormality based on a prescribed abnormality determination criterion.

* * * * *